US007625917B2

(12) United States Patent
Turpin et al.

(10) Patent No.: US 7,625,917 B2
(45) Date of Patent: *Dec. 1, 2009

(54) THIOLESTERS AND USES THEREOF

(76) Inventors: James A. Turpin, 3712 Basford Rd., Frederick, MD (US) 21703; Yongsheng Song, 140 Mill St., #15-107, East Haven, CT (US) 06512; Ettore Appella, 4112 Aspen St., Chevy Chase, MD (US) 20815; John K. Inman, 9200 Wadsworth Dr., Bethesda, MD (US) 20817; David G. Covell, 4307 Stanford St., Chevy Chase, MD (US) 20815; William G. Rice, 87 Mill Rd., Madison, CT (US) 06443; Anders Wallqvist, 102 E. 7th St., Frederick, MD (US) 21701; Andrew Maynard, 39 York Rd., Wilmington, DE (US) 19803; Mingjun Huang, 11621 Greenlane Dr., Rockville, MD (US) 20854

( * ) Notice: Subject to any disclaimer, the term of this patent is extended or adjusted under 35 U.S.C. 154(b) by 761 days.

This patent is subject to a terminal disclaimer.

(21) Appl. No.: 10/738,062

(22) Filed: Dec. 16, 2003

(65) Prior Publication Data
US 2004/0132785 A1 Jul. 8, 2004

Related U.S. Application Data

(63) Continuation of application No. 09/701,451, filed on May 16, 2001, now Pat. No. 6,706,729.

(60) Provisional application No. 60/089,842, filed on Jun. 19, 1998.

(51) Int. Cl.
 A61K 31/435 (2006.01)
 A61K 39/12 (2006.01)
(52) U.S. Cl. .................. 514/277; 546/1; 546/298; 435/5; 424/204.1; 514/706
(58) Field of Classification Search .............. 424/204.1; 435/5; 514/277, 354, 298; 546/298
 See application file for complete search history.

(56) References Cited

U.S. PATENT DOCUMENTS 5,541,317 A 7/1996 Hirai et al.

FOREIGN PATENT DOCUMENTS

WO WO 96/04242 2/1996
WO WO 96/09406 3/1996
WO WO 96/38144 12/1996

OTHER PUBLICATIONS

Aldovini A., and R.A. Young, "Mutations of RNA and protein sequences involved in human immunodeficiency virus type 1 packaging result in production of noninfectious virus," *J Virol*, 64(5):1920-6 (1990).

Ausubel, (ed.), *Current Protocols in Molecular Biology*, Greene Publishing and Wiley-Interscience, New York (1987).
Baggaley, et al., "Inhibitors of blood platelet aggregation. Effects of some 1,2-benzisothiazol-3-ones on platelet responsiveness to adenosine diphosphate and collagen," *J Med Chem*, 28(11):1661-7 (1985).
Berg, J.M., "Potential metal-binding domains in nucleic acid binding proteins," *Science*, 232(4749):485-7 (1986).
Bess, et al., "Tightly bound zinc in human immunodeficiency virus type 1, human T-cell leukemia virus type I, and other retroviruses," *J Virol*, 66(2):840-7 (1992).
Birnbaum, Journal of Biological Chemistry 194:455-470 (1952).
Buckheit, et al., "Potent and specific inhibition of HIV envelope-mediated cell fusion and virus binding by G quartet-forming oligonucleotide (ISIS 5320)," *AIDS Res Hum Retroviruses*, 10(11):1497-506 (1994).
Buki, et al., "Destabilization of Zn2+ coordination in ADP-ribose transferase (polymerizing) by 6-nitroso-1,2-benzopyrone coincidental with inactivation of the polymerase but not the DNA binding function," *FEBS Lett*, 290(1-2):181-5 (1991).
Chance, et al., "Extended x-ray absorption fine structure studies of a retrovirus: equine infectious anemia virus cysteine arrays are coordinated to zinc," *Proc Natl Acad Sci USA*, 89(21):10041-5 (1992).
Dannull, et al., "Specific binding of HIV-1 nucleocapsid protein to PSI RNA in vitro requires N-terminal zinc finger and flanking basic amino acid residues," *EMBO J*, 13(7):1525-33 (1994).
Demene, et al., "1H NMR structure and biological studies of the His23→Cys mutant nucleocapsid protein of HIV-1 indicate that the conformation of the first zinc finger is critical for virus infectivity," *Biochemistry*, 33(39):11707-16 (1994).
Edwards, et al.,"Large porous particles for pulmonary drug delivery," *Science*, 276(5320):1868-71 (1997).
Fehrmann, et al., "Intracisternal A-type particles express their proteinase in a separate reading frame by translational frameshifting, similar to D-type retroviruses," *Virology*, 235(2):352-9 (1997).
Flo, et al., "Longitudinal study of cytomegalovirus antibodies in individuals infected with the human immunodeficiency virus,"*Eur J Clin Microbiol Infect Dis*, 14(6):504-11 (1995).
Gaind, Sehgal and Ray; *Indian Chem. Soc.* 18:209 (1941).
Geretti, et al., "Cytotoxic T lymphocytes in AIDS pathogenesis: lessons to be learned from the macaque model of simian immunodeficiency virus infection," *J Gen Virol*, 79 ( Pt. 3):415-21.
Gilman et al. (eds), *Organic Syntheses Collective Volumes*, John Wiley & Sons, Inc., NY.
Gorelick, et al., "Noninfectious human immunodeficiency virus type 1 mutants deficient in genomic RNA," *J Virol*, 64(7):3207-11 (1990).
Grossman and Coburn, (eds), *Capillary Electrophoresis, Theory and Practice* (Academic Press, Inc. 1992.
Hashida, et al., "More reliable diagnosis of infection with human immunodeficiency virus type 1 (HIV-1) by detection of antibody IgGs to pol and gag proteins of HIV-1 and p24 antigen of HIV-1 in urine, saliva, and/or serum with highly sensitive and specific enzyme immunoassay (immune complex transfer enzyme immunoassay): a review," *J Clin Lab Anal*,11(5):267-86 (1997).

(Continued)

*Primary Examiner*—Sreeni Padmanabhan
*Assistant Examiner*—Shobha Kantamneni
(74) *Attorney, Agent, or Firm*—Cantor Colburn LLP

(57) ABSTRACT

This invention pertains to the discovery of a novel family of thiolesters and uses thereof. Also provided for are viricidal compounds and pharmaceutical formulations comprising these novel thiolesters. The invention also provides thiolester-inactivated viruses and thiolester-complexed viral proteins.

8 Claims, No Drawings

OTHER PUBLICATIONS

Henderson, et al., "Gag proteins of the highly replicative MN strain of human immunodeficiency virus type 1: posttranslational modifications, proteolytic processings, and complete amino acid sequences," *J Virol*, 66(4):1856-65 (1992).

Horstmann, *Eur. Journal Med. Chem. Chim. Ther.*, 12:387-391 (1977).

Huang, et al., "Anti-HIV agents that selectively target retroviral nucleocapsid protein zinc fingers without affecting cellular zinc finger proteins," *J Med Chem*, 41(9):1371-81 (1998).

Huang, et al., "Effect of mutations in the nucleocapsid protein (NCp7) upon Pr160(gag-pol) and tRNA(Lys) incorporation into human immunodeficiency virus type 1," *J Virol*, 71(6):4378-84 (1997).

Humphrey, et al., "Removal of human immunodeficiency virus type 1 (HIV-1) protease inhibitors from preparations of immature HIV-1 virions does not result in an increase in infectivity or the appearance of mature morphology," *Antimicrob Agents Chemother*, 41(5):1017-23 (1997).

Jacks, et al., "Characterization of ribosomal frameshifting in HIV-1 gag-pol expression," *Nature*, 331(6153):280-3 (1988).

Karacostas, et al., "Overexpression of the HIV-1 gag-pol polyprotein results in intracellular activation of HIV-1 protease and inhibition of assembly and budding of virus-like particles," *Virology*, 193(2):661-71 (1993).

Karpel, et al,"Interactions of retroviral structural proteins with single-stranded nucleic acids," *J Biol Chem*, 262(11):4961-7 (1987).

Katz, *J. Organic Chemistry*, 18:1380-1402 (1953).

Lapadat-Tapolsky, et al., "Possible roles of HIV-1 nucleocapsid protein in the specificity of proviral DNA synthesis and in its variability," *J Mol Biol*, 268(2):250-60 (1997).

Lee, et al., "Analysis of the S3 and S3' subsite specificities of feline immunodeficiency virus (FIV) protease: development of a broad-based protease inhibitor efficacious against FIV, SIV, and HIV in vitro and ex vivo," *Proc Natl Acad Sci USA*, 95(3):939-44 (1998).

Lu, Y., "HIV-1 vaccine candidate evaluation in non-human primates," *Crit Rev Oncog*, 8(2-3):273-91 (1997).

McDonnell, et al., "Azodicarbonamide inhibits HIV-1 replication by targeting the nucleocapsid protein," *Nat Med*, 3(3):341-5 (1997).

McDonnell, et al., "Zinc ejection as a new rationale for the use of cystamine and related disulfide-containing antiviral agents in the treatment of AIDS," *J Med Chem*, 40(13):1969-76 (1997).

Mohri, et al., "Rapid turnover of T lymphocytes in SIV-infected rhesus macaques," *Science*, 279(5354):1223-7 (1998).

Nasser, et al., "Antiviral activity of influenza virus M1 zinc finger peptides," *J Virol*, 70(12):8639-44 (1996).

Neildez, et al., "Selective quasispecies transmission after systemic or mucosal exposure of macaques to simian immunodeficiency virus," *Virology*, 243(1):12-20 (1998).

Newman, et al., "Use of nonionic block copolymers in vaccines and therapeutics," *Crit Rev Ther Drug Carrier Syst*, 15(2):89-142 (1998).

Patton, J.,"Breathing life into protein drugs," *Nat Biotechnol*, 16(2):141-3 (1998).

Putney, S.D. and P.A. Burke, "Improving protein therapeutics with sustained-release formulations," *Nat Biotechnol*, 16(2):153-7 (1998).

*Remington's Pharmaceutical Sciences*, Maack Publishing Co., Easton PA, including Ch. 37-39.

Rice, et al., "Evaluation of selected chemotypes in coupled cellular and molecular target-based screens identifies novel HIV-1 zinc finger inhibitors," *J Med Chem*, 39(19):3606-16.

Rice, et al., "Inhibition of HIV-1 infectivity by zinc-ejecting aromatic C-nitroso compounds," *Nature*, 361(6411):473-5 (1993).

Rice, et al., "Inhibition of multiple phases of human immunodeficiency virus type 1 replication by a dithiane compound that attacks the conserved zinc fingers of retroviral nucleocapsid proteins," *Antimicrob Agents Chemother*, 41(2):419-26 (1997).

Rice, et al., "Inhibitors of HIV nucleocapsid protein zinc fingers as candidates for the treatment of AIDS," *Science*, 270(5239):1194-7 (1995).

Rice, et al., "The site of antiviral action of 3-nitrosobenzamide on the infectivity process of human immunodeficiency virus in human lymphocytes," *Proc Natl Acad Sci USA*, 90(20):9721-4 (1993).

Ronwin, *Journal of Organic Chemistry*, 18:127 (1953).

Rossio, *HIV Pathogenesis and Treatment:Keystone Symposium on Molecular and Cellular Biology*, Abstract #4082 (1998).

Sambrook, et al., *Molecular Cloning A Laboratory Manual (2nd Ed.)*, vol. 1-3, Cold Spring Harbor Laboratory, Cold Spring harbor, New York, (1989).

Schwiebert, R.S., and P.N. Fultz, "Severe combined immunodeficient mice engrafted with macaque peripheral blood leukocytes support replication of SIVsmm," *AIDS Res Hum Retroviruses*, 14(3):269-74 (1998).

South, et al., "Zinc fingers and molecular recognition. Structure and nucleic acid binding studies of an HIV zinc finger-like domain," *Biochem Pharmacol*, 40(1):123-9 (1990).

South, T.L. and M.F. Summers, "Zinc- and sequence-dependent binding to nucleic acids by the N-terminal zinc finger of the HIV-1 nucleocapsid protein: NMR structure of the complex with the Psi-site analog, dACGCC," *Protein Sci*, 2(1):3-19 (1993).

South, T.L. and M.F. Summers, "Zinc fingers," *Adv Inorg Biochem*, 8:199-248 (1990).

Summers, et al., "Nucleocapsid zinc fingers detected in retroviruses: EXAFS studies of intact viruses and the solution-state structure of the nucleocapsid protein from HIV-1," *Protein Sci*, 1(5):563-74 (1992).

Tokunaga, et al., "Inhibition of human immunodeficiency virus type 1 virion entry by dominant-negative Hck," *J Virol*, 72(7):6257-9 (1998).

Tummino, et al., "The human immunodeficiency virus type 1 (HIV-1) nucleocapsid protein zinc ejection activity of disulfide benzamides and benzisothiazolones: correlation with anti-HIV and virucidal activities," *Antimicrob Agents Chemother*, 41(2):394-400 (1997).

Turpin, et al., "Reverse transcription of human immunodeficiency virus type 1 is blocked by retroviral zinc finger inhibitors," *Antiviral Chem. Chemother.*, 8:60-67.

Turpin, et al., "Synthesis and biological properties of novel pyridinioalkanoyl thiolesters (PATE) as anti-HIV-1 agents that target the viral nucleocapsid protein zinc fingers," *J Med Chem*, 42(1):67-86 (1999).

Turpin, et al., "Inhibition of acute-, latent-, and chronic-phase human immunodeficiency virus type 1 (HIV-1) replication by a bistriazoloacridone analog that selectively inhibits HIV-1 transcription," *Antimicrob Agents Chemother*, 42(3):487-94 (1998).

Turpin, et al., "Inhibitors of human immunodeficiency virus type 1 zinc fingers prevent normal processing of gag precursors and result in the release of noninfectious virus particles," *J Virol*, 70(9):6180-9 (1996).

Ullman, et al., "Predicted alpha-helix/beta-sheet secondary structures for the zinc-binding motifs of human papillomavirus E7 and E6 proteins by consensus prediction averaging and spectroscopic studies of E7," *Biochem J*, 319 ( Pt 1):229-39 (1996).

Venuti, et al., "Synthesis and biological evaluation of omega-(N,N,N-trialkylammonium)alkyl esters and thioesters of carboxylic acid nonsteroidal antiinflammatory agents," *Pharm Res*, 6(10):867-73 (1989).

Vogt, P.K. "Historical introduction to the general properties of retroviruses," in *Retroviruses*, eds. J.M. Coffin, S.H. Hughes and H.E. Varmus, Cold Spring Harbor Laboratory Press, pp. 1-26; Murphy et al. (eds.) (1997).

Weislow, et al., "New soluble-formazan assay for HIV-1 cytopathic effects: application to high-flux screening of synthetic and natural products for AIDS-antiviral activity," *J Natl Cancer Inst*, 81(8):577-86 (1989).

Wu, et al.,"Structural basis for specificity of retroviral proteases," *Biochemistry*, 37(13):4518-26 (1998).

Yamashita, et al., "Multiple-step method for making exceptionally well-oriented liquid-crystalline sols of macromolecular assemblies," *J Mol Biol*, 278(3):609-15 (1998).

THIOLESTERS AND USES THEREOF

CROSS REFERENCE TO RELATED APPLICATIONS

This application is a continuation of U.S. patent application Ser. No. 09/701,451, filed May 16, 2001 now U.S. Pat. No. 6,706,729, which claims the benefit of Application No. 60/089,842, filed Jun. 19, 1998, which are herein incorporated by reference in their entirety for all purposes.

FIELD OF THE INVENTION

This invention pertains to the field of virology and antiviral therapeutics. In particular, this invention pertains to the discovery of a novel family of thiolesters and uses thereof.

BACKGROUND OF THE INVENTION

Viruses, especially retroviruses such as HIV, can become rapidly resistant to drugs used to treat the infection. This extreme adaptability of retroviruses is due to the high error rate of the reverse transcriptase enzyme responsible for transcribing its RNA genome. HIV is an example of such a hyper-mutable virus. It has diverged into two major species, HIV-1 and HIV-2, each of which has many clades, subtypes and drug resistant variations.

Strategies for coping with emergence of viral drug-resistant strains include combination drug therapies (Lange (1996) *AIDS* 10 Suppl 1:S27-S30). Drugs against different viral proteins and drugs against multiple sites on the same protein are commonly used as a strategy to overcome the adaptability of the virus. Combination therapies for retroviruses, using, e.g., protease inhibitors and nucleoside analogues, such as AZT, ddI, ddC and d4T, can become ineffectual; the virus develops complete resistance in a relatively short period of time (Birch (1998) *AIDS* 12:680-681; Roberts (1998) *AIDS* 12:453-460; Yang (1997) *Leukemia* 11 Suppl 3:89-92; Demeter (1997) *J. Acquir. Immune Defic. Syndr. Hum. Retrovirol.* 14(2):136-144; Kuritzkes (1996) *AIDS* 10 Suppl 5:S27-S31). Furthermore, no effective anti-retroviral vaccine is currently available (Bolognesi (1998) *Nature* 391: 638-639; Bangham (1997) *Lancet* 350:1617-1621).

The HIV-1 caused AIDS epidemic began about 18 years ago. Since then the number of new cases have increased over time. By the end of 1994, 1,025,073 AIDS cases had been reported to the WHO, with a 20% increase in the number of cases since December, 1993 (Galli (1995) *Q. J. Nucl. Med.* 39:147-155). By the year 2000, the WHO predicts that there will be 30 to 40 million cumulative HIV-1 infections in the world (Stoneburner (1994) *Acta Paediatr. Suppl.* 400:1-4). Thus, there exists a great need for compounds effective against retroviruses such as HIV-1. The present invention fulfills these and other needs.

SUMMARY OF THE INVENTION

The invention provides a novel genus of compositions comprising a thiolester having a chemical structure selected from the group consisting of:

a thiolester having a formula selected from the group consisting of Template I and Template II, wherein Template I and Template II have the structures

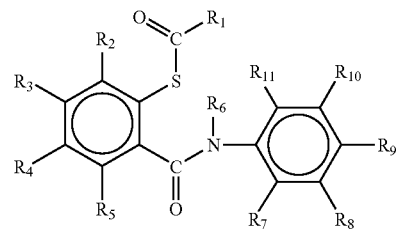
Template I

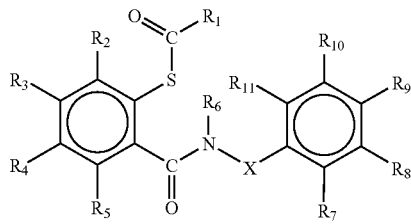
Template II wherein X is a member selected from the group consisting of alkyl, substituted alkyl, aryl, and substituted aryl groups; $R_1$ is —Y-Z-, wherein Y is selected from the group consisting of —$(CH_2)_m$—, wherein m is an integer from 1 to 6,

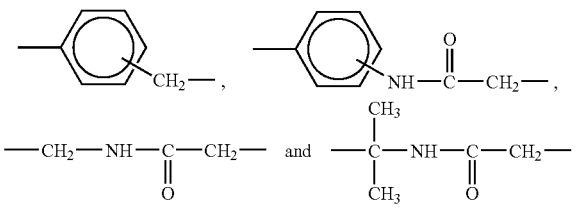

where Z is selected from the group consisting of dialkyl or aryl or alkylaryl sulfonium (Z1), trialkyl or aryl or alkylaryl ammonium (Z2), trialkyl or aryl or alkylaryl phosphonium (Z3), or pyridinio (Z4) having the structure

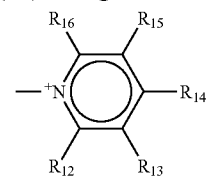

wherein $R_{12}$, $R_{13}$, $R_{14}$, $R_{15}$, and $R_{16}$, are members independently selected from the group consisting of H—, —C(=O)$NH_2$, and substituted carboxamide groups, or, $R_1$ is selected from the group consisting of alkyl, substituted alkyl, -aryl, substituted aryl, -arylalkyl, -Ph-$CH_3$, arylalkoxy, -Ph-$OCH_3$, nitroaryl, -Ph-$NO_2$, and —$(CH_2)_n$—X groups, where X is a halogen, and n is an integer from 1 to 6;

$R_2$ is selected from the group consisting of —H, —$CH_3$, —C(=O)$NH_2$ and —C(=O)$OCH_3$ groups;

$R_3$, $R_4$ and $R_5$ are members independently selected from the group consisting of H, a halogen, —$NO_2$, —C(=O)$ONH_2$, and —C(=O)$OCH_3$ groups;

$R_6$ is selected from the group consisting of —H, alkyl, —$CH_3$, substituted alkyl, aryl, substituted aryl, and arylalkyl groups;

$R_7$, $R_8$, $R_9$, $R_{10}$ and $R_{11}$ are H except either $R_7$, $R_8$, or $R_9$ can be (O=S=O)-G' wherein G' is selected from the group consisting of —$NH_2$, —NH-alkyl, —NH-aryl, —NH-acyl, aryl-$NH_2$, nitroaryl, aryl-NH-acyl, and aryl-NH-alkyl groups;

a thiolester having a formula selected from the group consisting of Template III and Template IV, wherein Template III and Template IV have the structures

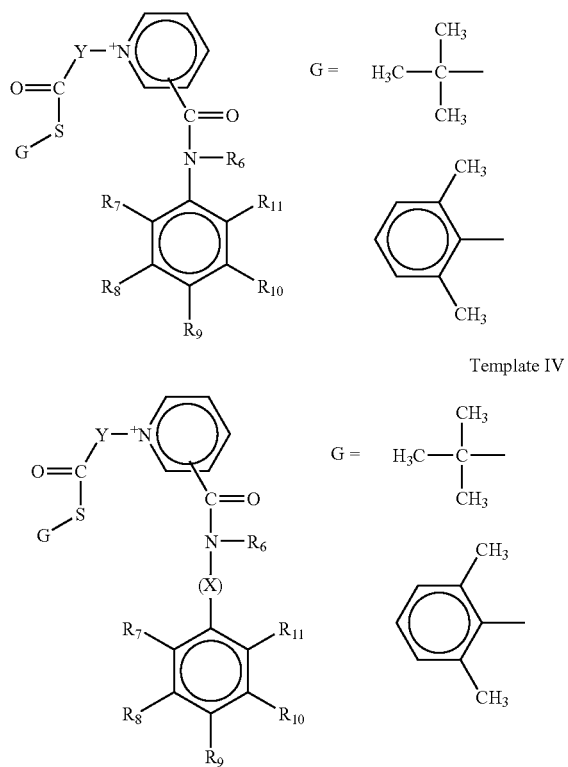

Template III

Template IV wherein G is selected from the group consisting of alkyl, substituted alkyl, aryl, substituted aryl, and alkylaryl groups, $R_6$ is selected from the group consisting of —H, alkyl, —$CH_3$, substituted alkyl, aryl, substituted aryl, and arylalkyl groups;

$R_7$, $R_8$, $R_9$, $R_{10}$ and $R_{11}$ are H except either $R_7$, $R_8$, or $R_9$ can be (O=S=O)-G' wherein G' is selected from the group consisting of —$NH_2$, —NH-alkyl, —NH-aryl, —NH-acyl, aryl-$NH_2$, nitroaryl, aryl-NH-acyl, and aryl-NH-alkyl groups;

a thiolester having a formula selected from the group consisting of Template V and Template VI, wherein Template V and Template VI have the structures Template V

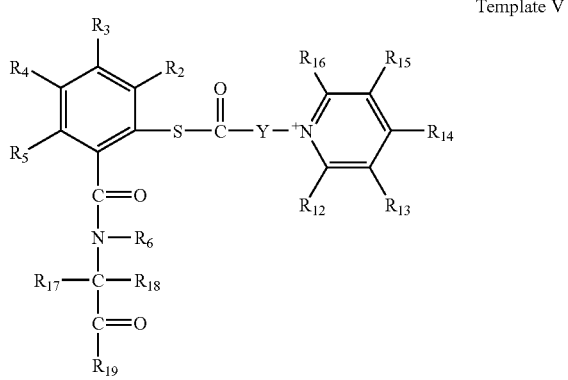

Template VI

-continued wherein n is any integer, $R_2$ through $R_5$, $R_6$, and $R_{12}$ through $R_{16}$ are defined as above, Y is as defined above, $R_{17}$ is —H or —$CH_3$, $R_{18}$ is —H, —$CH_3$, alkyl, aryl, arylalkyl, or an amino acid side chain, wherein the stereochemical configuration about the carbon atom to which $R_{18}$ is attached may be R or S, $R_{19}$ is —OH, —$NH_2$, N-substituted amide nitrogen, or an ester group (—OR);

a thiolester having a formula of Template VII with the structure

Template VII wherein $R_0$ is any substituted or unsubstituted aryl or heteroaryl ring system attached directly to the sulfur atom, Y and $R_{12}$ through $R_{16}$ are defined as above; and a pyridinioalkanoyl thiolester having a formula wherein m is an integer from 1 to 6, n is 0 or an integer from 1 to 6, and R is selected from the group consisting of alkyl, substituted alkly, aryl, substituted aryl, akylaryl, carboxamide, carboxamido, substituted carboxamide, substituted carboxamido, —$NH_2$ groups, and substituted —$NH_2$ groups.

In alternative embodiments, in the thiolester, X is a member selected from the group consisting of —$(CH_2)m$-, wherein m is an integer 1 to 6, and —$CH_2(C=O)NH$—; $R_1$ is selected from the group consisting of —$CH_3$, —$(CH_2)_n$—$CH_3$, —$CH(CH_3)_2$, —$C(CH_3)_3$, —$(CH_2)_n$—Cl, —$(CH_2)_n$—Br, and —$(CH_2)_n$—I groups; G is selected from the group consisting of —$CH(CH_3)_2$, —$C(CH_3)_3$; and 2,6-dimethyl phenyl groups; and, the pyridinioalkanoyl thiolester R group is selected from the group consisting of —NHC(=O)CH$_3$, —C$_6$H$_4$NO$_2$, —C$_6$H$_4$NHSO$_2$CH$_2$C$_6$H$_4$NO$_2$ and —C$_6$H$_4$NHCOCH$_3$ groups. The pyridinioalkanoyl thiolester can have a structure wherein m is the integer 4 and n=0 or the integer 1 or 2.

In one embodiment, the thiolester of the invention is capable of dissociating a metal ion from a zinc finger in vitro. In another embodiment the thiolester of the invention has antiviral activity.

The invention provides a method for dissociating a metal ion from a zinc finger-containing protein, the method comprising the step of contacting said zinc finger with a thiolester of the invention. In alternative embodiments, the metal ion is a zinc ion; the zinc finger comprises a viral protein; the viral protein is a nucleocapsid protein, a Gag protein, or a Gag-Pol protein; and, the zinc finger-containing protein is incorporated into an intact virus.

In one embodiment, in the method for dissociating a metal ion from a zinc finger-containing protein, the contacting of said virus with said compound is performed in vitro. The contacting of said virus with said compound can also be performed in vivo. The zinc finger can comprises a retroviral protein derived from a avian sarcoma and leukosis retroviral group, a mammalian B-type retroviral group, a human T cell leukemia and bovine leukemia retroviral group, a D-type retroviral group, a murine leukemia-related group, or a lentivirus group. The retroviral protein can be from an HIV-1, an HIV-2, an SIV, a BIV, an EIAV, a Visna, a CaEV, an HTLV-1, a BLV, an MPMV, an MMTV, an RSV, an MuLV, a FeLV, a BaEV, or an SSV retrovirus. This method can further comprising detecting the dissociation of said metal ion from the zinc finger of said viral protein. The detection of the dissociation of said metal ion from the zinc finger can be carried out using a method selected from the group consisting of capillary electrophoresis, immunoblotting, Nuclear Magnetic Resonance (NMR), high pressure liquid chromatography (HPLC), detecting release of radioactive zinc-65, detecting fluorescence, and detecting gel mobility shift.

The invention also provides a method for inactivating a virus, said method comprising contacting said virus with a compound of the invention, wherein contacting said virus with the compound inactivates the virus. In this method, the compound can dissociates a zinc ion from a zinc finger. The virus can be a retrovirus derived from a avian sarcoma and leukosis retroviral group, a mammalian B-type retroviral group, a human T cell leukemia and bovine leukemia retroviral group, a D-type retroviral group, a murine leukemia-related group, or a lentivirus group. The retrovirus can be an HIV-1, an HIV-2, an SIV, a BIV, an EIAV, a Visna, a CaEV, an HTLV-1, a BLV, an MPMV, an MMTV, an RSV, an MuLV, a FeLV, a BaEV, or an SSV retrovirus.

In the method for inactivating a virus, the contacting of the virus with the compound can be performed in vivo. In this embodiment, the compound can be administered to inhibit the transmission of the virus. The compound can be administered intra-vaginally or intra-rectally to inhibit the transmission of the virus. The compound can be administered to a human as a pharmaceutical formulation. The compound can be administered to an animal as a veterinary pharmaceutical formulation. The method can further comprises contacting the virus with a non-thiolester anti-retroviral agent. The anti-retroviral agent can be a nucleotide analogue or a protease inhibitor. The nucleotide analogue can be AZT, ddCTP or DDI.

In the method for inactivating a virus, the contacting of the virus with the compound can be performed in vitro. In this embodiment of the method, the contacting of the retrovirus with the compound can be performed in a blood product, blood plasma, nutrient media, protein, a pharmaceutical, a cosmetic, a sperm or oocyte preparation, cells, cell cultures, bacteria, viruses, food or drink.

The invention also provides an isolated and inactivated virus, wherein the virus is inactivated by a method comprising contacting said virus with a thiolester of the invention, wherein contacting the virus with the thiolester inactivates the virus. The isolated and inactivated virus can further comprise a vaccine formulation. The isolated and inactivated virus can be a retrovirus derived from a avian sarcoma and leukosis retroviral group, a mammalian B-type retroviral group, a human T cell leukemia and bovine leukemia retroviral group, a D-type retroviral group, a murine leukemia-related group, or a lentivirus group. The virus can be an HIV-1, an HIV-2, an SIV, a BIV, an EIAV, a Visna, a CaEV, an HTLV-1, a BLV, an MPMV, an MMTV, an RSV, an MuLV, a FeLV, a BaEV, or an SSV retrovirus.

The invention also provides a method of selecting a compound capable of dissociating a metal ion chelated with a zinc finger of a viral protein, said method comprising: contacting the zinc finger with a thiolester, and detecting the dissociation of said metal ion from the zinc finger of said viral protein. In this method, the metal ion can be a zinc ion. In this method, the detection of the dissociation of said metal ion from the zinc finger can be carried out using capillary electrophoresis, immune-blotting, Nuclear Magnetic Resonance (NMR), high pressure liquid chromatography (HPLC), detecting release of radioactive zinc-65, detecting fluorescence, or detecting gel mobility shift.

The invention also provides a kit for selecting a compound capable of dissociating a metal ion from a zinc finger of a viral protein, the kit comprising a retroviral protein and instructions for detecting the dissociation of said metal ion from the viral protein, the instructions comprising directions for the selection of a thiolester of the invention. In the kit, the viral protein can be supplied with a zinc ion chelated with the zinc finger of said viral protein. The viral protein can be incorporated in an intact retrovirus. The zinc finger can be derived from a avian sarcoma and leukosis retroviral group, a mammalian B-type retroviral group, a human T cell leukemia and bovine leukemia retroviral group, a D-type retroviral group, a murine leukemia-related group, or a lentivirus group. The zinc finger can be derived from an HIV-1, an HIV-2, an SIV, a BIV, an EIAV, a Visna, a CaEV, an HTLV-1, a BLV, an MPMV, an MMTV, an RSV, an MuLV, a FeLV, a BaEV, or an SSV retrovirus. In the kit, the instructions can be are directed to detecting the dissociation of said metal ion from said protein using capillary electrophoresis, immune-blotting, Nuclear Magnetic Resonance (NMR), high pressure liquid chromatography (HPLC), detecting release of radioactive zinc-65, detecting fluorescence or detecting a gel mobility shift.

The invention also provides a viricidal composition comprising a thiolester of the invention. In one embodiment, the viricidal composition further comprises blood plasma, nutrient media, protein, a pharmaceutical, a cosmetic, a sperm or oocyte preparation, cells, cell cultures, bacteria, viruses, food or drink.

The invention also provides a pharmaceutical formulation comprising a thiolester of the invention. The pharmaceutical formulation can further comprise a pharmaceutical excipient.

A further understanding of the nature and advantages of the present invention may be realized by reference to the remaining portions of the specification and claims.

All publications, electronic databases, patents and patent applications cited herein are hereby expressly incorporated by reference for all purposes.

DETAILED DESCRIPTION

The efficacy of most antiviral agents is limited because it is common that, under selection pressure, viruses mutate to drug-resistant strains. Development of drug resistance is a survival strategy particularly pronounced amongst retroviruses because of their ability to rapidly mutate. Viral structures necessary for viability and growth are good drug targets because their inactivation cannot be easily overcome by mutation. Viral structures essential for replication and viability are good targets for drug development. The utility of these targets can be further enhanced if the structures are mutationally intolerant. Furthermore, these structures maybe conserved and/or maintained between virus families, groups or genuses.

The invention provides a novel genus of thiolester compositions. These thiolesters are capable of inactivating viruses by a variety of mechanisms, particularly by complexing with metal ion-complexing zinc fingers. In a preferred embodiment, the thiolester compositions of the invention inactivate retroviruses. Typically, this inactivation is effected when the thiolester contacts the virus' nucleocapsid, or other zinc finger containing, proteins. An important aspect of these novel compositions is that they are not effected (i.e., their activity is not greatly diminished in vivo) by the reducing environment of biological fluids. Thus, they are important therapeutic reagents in the treatment of viral, especially retroviral, agents. The viricidal activity of the compositions of the invention are also useful in in vitro applications, such as e.g., making killed viruses to used as, e.g., reagents or vaccines, and as sterilizing reagents.

A "zinc finger" motif is a highly conserved and essential structure found in many viruses, especially retroviruses. The Gag and Gag-Pol proteins in the Retroviridae, except for Spumaviruses, contain a highly conserved zinc finger motif (CCHC) within the nucleocapsid p7 (NCp7) protein portion of the polyprotein (see definitions, below). The absolute conservation of the metal chelating cysteine and histidine residues along with other residues of the protein and its in participation in essential functions during early and late virus replication identifies this feature as an antiviral target. Mutations of the chelating residues in the zinc fingers yield a non-infectious virus. Because zinc fingers are identical in most retroviruses, reagents able to inhibit its function have the potential of being broad spectrum anti-viral therapeutic drugs.

HIV-1's nucleocapsid (NC) protein, NCp7, contains two zinc fingers separated by only seven amino acids (Henderson (1992) *J. Virol.* 66:1856). Both fingers are essential for infectivity (Aldovini (1990) *J. Virol.* 64:1920; Gorelick (1990) *J. Virol.* 64:3207). Thus, HIV-1 nucleocapsid is a particularly vulnerable target for zinc finger inactivating reagents. All evidence points toward complete conservation of the chelating residues and some other key residues within the finger. Mutation of any of these residues results in loss or severe compromise of virus infectivity. Even mutations which maintain metal ion chelating properties of the finger (CCHC to CCHH or CCCC) result in loss of infectivity. Thus, there is no known evidence for a mutational pathway of single or multiple mutations leading to restoration of protein activity.

Various C-nitroso compounds and disulfide-containing compounds, such as cystamine, thiamine disulfide, and disulfiram, can oxidize zinc finger cysteine thiolates and induce intra- and inter-molecular disulfide cross-linking, see, e.g., McDonnell (1997) *J. Med. Chem.* 40:1969-1976; Rice (1997) *Nature Medicine* 3:341-345; Rice (1997) *Antimicrob. Agents and Chemotherapy* 41:419-426; Rice (1996) *J. Med. Chem.* 39:3606-3616; Rice (1996) *Science* 270:1194-1197; Rice (1993) *Proc. Natl. Acad. Sci. USA* 90:9721-9724; Rice (1993) *Nature* 361:473-475. See also Henderson, et al., WO 96/09406. Cysteine thiols in each of the two zinc fingers are rapidly attacked by reagents such as $Cu^{+2}$, $Fe^{+3}$, C-nitroso compounds, disulfides, maleimides, alpha-halogenated ketones and nitric oxide derivatives, with simultaneous loss of the native protein structure. For example, treatment of intact HIV-1 with an oxidizing agent, such as 3-nitrosobenzamide, a C-nitroso compound, induces disulfide linkage of the nucleocapsid protein and inactivates viral infectivity through oxidation of the zinc fingers (Rice (1993) *Nature* 361:473; Rice (1993) *Proc. Natl. Acad. Sci. USA* 90:9721-9724). C-nitroso compounds can also inactivate eukaryotic CCHC zinc finger containing poly(ADP-ribose) polymerase (Buki (1991) *FEBS Letters* 290:181). However, these compounds tend to be toxic, have poor solubility and bioavailability, and are reduced and inactivated in biological solutions.

The novel thiolesters of the invention interact with the zinc finger via their thiolester moiety rather than an electrophilic S—S moiety. The resultant thiolesters lack S—S electrophilic moieties. Less nucleophilic groups are used to target zinc finger motifs. As a result, they have greatly enhanced properties as compared to many disulfide reagents. They have reduced cellular toxicity. They have enhanced antiviral activity and better reactivity with zinc finger moieties, particularly, the zinc finger on HIV-1's NCp7 nucleocapsid protein. The thiolesters of the invention have enhanced aqueous solubilities. They maintain zinc finger reactivity in the presence of reducing agents. The combination of improved characteristics, especially resistance to reduction in a biological solution, in the thiolesters of the invention clearly enhances their use in in vitro, in vivo and therapeutic applications.

Definitions

To facilitate understanding the invention, a number of terms are defined below.

As used herein, the term "alkyl" is used to refer to a branched or unbranched, saturated or unsaturated, monovalent hydrocarbon radical having from 1-30 carbons and preferably, from 4-20 carbons and more preferably from 6-18 carbons. When the alkyl group has from 1-6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls." "Substituted alkyl" refers to alkyl as just described including one or more functional groups such as lower alkyl, aryl, acyl, halogen (i.e., alkylhalos, e.g., CF3), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon of the alkyl moiety. Additionally, these groups may be pendent from, or integral to, the alkyl chain.

The term "alkoxy" is used herein to refer to the COR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and are as described herein for "alkyl groups."

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl." "Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "arylalkyl" is used herein to refer to a subset of "aryl" in which the aryl group is further attached to an alkyl group, as defined herein.

"Contacting" refers to the act of bringing components of a reaction into adequate proximity such that the reaction can occur. More particularly, as used herein, the term "contacting" can be used interchangeably with the following: combined with, added to, mixed with, passed over, flowed over, etc.

As used herein, the term "Gag-Pol protein" refers to the polyprotein translation product of HIV-1 or other retroviruses, as described, e.g., by Fehrmann (1997) *Virology* 235: 352359; Jacks (1988) *Nature* 331:280-283. The "Gag protein" is processed by a viral protease to yield mature viral proteins, see, e.g., Humphrey (1997) *Antimicrob. Agents Chemother.* 41:1017-1023; Karacostas (1993) *Virology* 193: 661-671.

The term "halogen" is used herein to refer to fluorine, bromine, chlorine and iodine atoms.

As used herein, "isolated," when referring to a molecule or composition, such as, for example, a thiolester of the invention, a thiolester-complexed polypeptide or virus, or a thiolester-inactivated virus, means that the molecule or composition is separated from at least one other compound, such as a protein, other nucleic acids (e.g., RNAs), or other contaminants with which it is associated in vivo or in its naturally occurring state. Thus, a compound, polypeptide or virion is considered isolated when it has been isolated from any other component with which it is naturally associated, e.g., cell membrane, as in a cell extract, serum, and the like. An isolated composition can, however, also be substantially pure. An isolated composition can be in a homogeneous state and can be in a dry or an aqueous solution. Purity and homogeneity can be determined, for example, using analytical chemistry techniques such as polyacrylamide gel electrophoresis (SDS-PAGE) or high performance liquid chromatography (HPLC).

As used herein, the term "nucleocapsid protein" or "NC protein" refers to the retroviral nucleocapsid protein, which is an integral part of the virion nucleocapsid, where it coats the dimeric RNA genome, as described by, e.g., Huang (1997) *J. Virol.* 71:4378-4384; Lapadat-Tapoisky (1997) *J. Mol. Biol.* 268:250-260. HIV-1's nucleocapsid protein is termed "NCp7," see also Demene (1994) *Biochemistry* 33:11707-11716.

The term "retrovirus" as used herein refers to viruses of the Retroviridae family, which typically have ssRNA transcribed by reverse transcriptase, as defined by, e.g., P. K. Vogt, "Historical introduction to the general properties of retroviruses," in Retroviruses, eds. J. M. Coffin, S. H. Hughes and H. E. Varmus, Cold Spring Harbor Laboratory Press, 1997, pp 1-26; Murphy et al. (eds.) Archives of Virology/Supplement 10, 586 pp (1995) Springer Verlag, Wien, N.Y.; and the web site for the Committee on International Taxonomy of Viruses, Virology Division of the International Union of Microbiology Society at http://www.ncbi.nlm.nih.gov/ICTV/ for viral classification and taxonomy. Retroviridae family members containing zinc finger motif-containing polypeptides and whose replication can be inhibited by the thiolesters of the invention include avian sarcoma and leukosis retroviruses (alpharetroviruses), mammalian B-type retroviruses (betaretrovirus) (e.g., mouse mammary tumor virus), human T cell leukemia and bovine leukemia retroviruses (deltaretroviruses) (e.g., human T-lymphotropic virus 1), murine leukemia-related group (gammaretroviruses), D-type retroviruses (epsilonretrovirus) (e.g., Mason-Pfizer monkey virus), and Lentiviruses. Lentiviruses include bovine, equine, feline, ovine/caprine, and primate lentivirus groups, such as human immunodeficiency virus 1 (HIV-1). Examples of particular species of viruses whose replicative capacity is affected by the thiolesters of the invention include HIV-1, HIV-2, SIV, BIV, EIAV, Visna, CaEV, HTLV-1, BLV, MPMV, MMTV, RSV, MuLV, FeLV, BaEV, and SSV retrovirus.

As used herein, the terms "thiolester" and "thioester" may be used interchangeably, and they refer to a chemical structure, G-S—(C=O)-G', wherein G and G' represent any two groupings of atoms; and any chemical structure consisting of an oxygen-based carbonyl group linked directly to a sulfur atom in the −2 oxidation state. The carbon and sulfur atoms, in turn, are linked to any two groupings of atoms; thus, G-S—(C=O)-G'.

As used herein, the term "zinc finger" refers to a polypeptide motif consisting of cysteines and/or histidines that coordinate metal ions giving rise to structures involved in protein/nucleic acid and/or protein/protein interactions. The thiolesters of the invention are capable of dissociating metal ions from a zinc finger in vitro. Typically, the metal ion is a divalent cation, such as zinc or cadmium. A zinc finger motif-containing protein is commonly a highly conserved and essential structure in viruses. Zinc finger motifs are found in human papilloma virus (HPV), particularly, HPV E6 and E7 proteins (see, e.g., Ullman (1996) *Biochem J.* 319:229-239), influenza virus (see, e.g., Nasser (1996) *J. Virol.* 70:8639-8644). In most subfamilies of Retroviridae, including avian sarcoma and leukosis retroviruses, mammalian B-type retroviruses, human T cell leukemia and bovine leukemia retroviruses, D-type retroviruses, and Lentiviruses, the invariable zinc finger motif is the most highly conserved structure. Retroviral nucleocapsid, Gag and Gag-Pol proteins have zinc finger motifs. In retroviruses, the zinc finger motif typically consists of 14 amino acids, with four residues being invariant: $\underline{C}ys(X)2\underline{C}ys(X)_4His(X)_4\underline{C}ys$ and thus is referred to as a "CCHC zinc finger" (Henderson (1981) *J. Biol. Chem.* 256: 8400). It chelates zinc through its histidine imidazole and cysteine thiolates (Berg (1986) *Science* 232:485; Bess (1992) *J. Virol.* 66:840; Chance (1992) *Proc. Natl. Acad. Sci. U.S.A.* 89:10041; South (1990) *Adv. Inorg. Biochem.* 8:199; South (1990) *Biochem. Pharmacol.* 40:123-129). CCHC zinc fingers perform essential functions in retroviral infectivity, such as packaging genomic RNA. They are also essential for early events in virus infection.

As used herein, the term "capable of dissociating a metal ion from a zinc finger in vitro or has antiviral activity" means a thiolester is within the scope of the invention if, using an in. vitro assay, several of which are described herein, it is capable of dissociating a metal ion from a zinc finger to any degree. Detecting the dissociation of a metal ion from a zinc finger can be carried out using, e.g., capillary electrophoresis, immunoblotting, Nuclear Magnetic Resonance (NMR), high pressure liquid chromatography (HPLC), detecting release of radioactive zinc-65, detecting fluorescence, and detecting gel mobility shift. The term also means that a thiolester is within the scope of the invention if it displays any antiviral activity in any assay, e.g., the XTT cytoprotection assay described herein. For example, a thiolester with any degree of measurable antiviral activity is within the scope of the invention even if no metal ion dissociation is detectable.

As used herein, the terms "inhibit the transmission of the virus" and "antiviral activity" means the ability of a thiolester to negatively effect viral replicative capacity in any way. Such inhibition of transmission, e.g., loss in replicative capacity, can be measured using any means known in the art. For example, a thiolester of the invention is inhibiting the transmission of the virus (having antiviral activity) if it diminishes a virus' ability to produce progeny, (when in the form of a virion) fuse with a cell, enter a cell, bud from a cell, survive intracellularly or extracellularly, reverse transcribe its RNA genome, translate viral proteins, process polyproteins with proteases, effect intracellular assembly of viral components into a capsid, and the like. The ability of a thiolester of the invention to inhibit the transmission of a virus is not limited by any chemical or biological mechanism or pathway. A thiolester can inhibit the transmission (decrease replicative capacity) of a virus by, e.g., binding to a nucleocapsid protein, such as NCp7; prevent binding of NCp7 to viral RNA or another nucleic acid; being involved in a specific chemical attack resulting in stable adduct formation; forming intracellular disulfide bonds as a result of collapse of unstable NCp7 compounds adducts; interacting with other conserved or non-conserved residues within the NCp7 protein which results in loss of function; and the like.

General Methods

The present invention provides a novel genus of thiolester compounds capable of dissociating a metal ion from a zinc finger in vitro. The skilled artisan will recognize that the thiolesters of the invention can be synthesized using a variety of procedures and methodologies, which are well described in the scientific and patent literature., e.g., Organic Syntheses Collective Volumes, Gilman et al. (Eds) John Wiley & Sons, Inc., NY; Venuti (1989) *Pharm Res.* 6:867-873. The invention can be practiced in conjunction with any method or protocol known in the art, which are well described in the scientific and patent literature. Therefore, only a few general techniques will be described prior to discussing specific methodologies and examples relative to the novel thiolesters and methods of the invention.

All organic reagents and intermediates were obtained from Sigma/Aldrich (St Louis, Mo.) and Lancaster Synthesis, Inc. (Windham, N.H.). Solvents and others chemicals were reagent grade. Structure and composition of all compounds were verified by $^1$H NMR and EI MS, and analyzed by silica layer TLC, eluting with methanol/acetic acid (6:4) for thiolesters, including the pyridinioalkanoyl thioester (PATE) chemotype, and chloroform/methanol (9:1) for the others.

The thiolesters of the invention are used to inactivate zinc finger containing retroviruses, such as HIV-1, by attacking the zinc fingers and ejecting the zinc therefrom. It will be readily apparent to those of skill in the art that once inactivated, the retrovirus can be used, for example, as vaccines, as prophylactics, or as components in standard ELISA assays for the diagnosis of retroviral infections. Making and using these novel compositions and methods can involve incorporating a variety of standard procedures and reagents. Kits for identifying compounds that can react with HIV-1 CCHC zinc fingers are also provided. In addition to the novel compositions of the invention, these kits incorporate a variety of standard procedures and reagents.

The following discussion of the general methods which can be used in conjunction with the present invention is intended for illustrative purposes only. Other alternative methods and embodiments will be apparent to those of skill in the art upon review of this disclosure.

Synthesis of Disulfide Benzamide Chemotype, Compound 2D

An exemplary means to synthesize compound 2D as described in Table 1 ("D" designated a dimer form, or "D form" as noted in Table 1) or N,N'-(2,2'-dithiodibenzoyl)-bis-sulfacetamide, follows. The starting material, 2,2'-dithiodibenzoyl chloride, was synthesized as described by Katz (1953) *J. Org. Chem* 18:1380-1402; Baggaley (1985) *J. Med. Chem.* 28:1661-1667. To a solution of sulfacetamide (13 g, 60 mmol) in pyridine (300 ml) was added dropwise a solution of 2,2'-dithiodibenzoyl chloride (as 85%, 8.1 g, 20 mmol) in 1,4-dioxane (100 ml) at room temp (RT). The clear, reddish-brown solution was stirred at RT overnight, then poured into vigorously stirred ethyl ether (1 L). The viscous liquid precipitate was separated from the ether phase, dissolved in N,N-dimethylformamide (DMF, approximately 50 ml), and added dropwise to 800 ml of vigorously stirred, aqueous 3 M HCl. The white precipitate was filtered off, washed with water and dried in vacuum. Yield, 11 g (78%). The crude product (1 g) was dissolved in hot ethanol (20 ml). The hot filtrate was added to stirred water (200 ml). The white precipitate was filtered off and dried. Yield was 0.85 grams (85%) of pure 2D. $^1$H NMR (DMSO-d$_6$), (12.08 (s, $^1$H, HNSO$_2$), 11.04 (s, 1H, HN-Ph), 8.01 (AB q , 4H, H-Ph), 7.87 (d, 1H, J=7.6 Hz, H-Ph), 7.81 (d, 1H, J=7.8 Hz, H-Ph), 7.59 (t, 1H, J=7.7 Hz, H-Ph), 7.46 (t, 1H, J=7.4 Hz, H-Ph), 1.97 (s, 3H, CH$_3$); EI MS m/z 699 (MH$^+$); Anal. Calcd (C$_{30}$H$_{26}$N$_4$O$_8$S$_4$): C, 51.56; H, 3.75; N, 8.02. Found: C, 51.34, H, 3.84, N, 8.05.

Synthesis of Benzoisothiazolone Chemotypes, Compounds 2B, 22, 31, 34

Exemplary means to synthesize benzoisothiazolone chemotypes, including compound 2B as described in Table 1 (the "B" designates the BITA, or benzoisothiazolone form) or N-[4-(3-oxo-3H-benz[d]isothiazol-2-yl)phenylsulfonyl] acetamide, follows. Two methods were used. In one method, to a solution of compound 2D (0.2 g, 0.28 mmol) in pyridine (2 ml) was added a solution of N-bromosuccinimide (0.18 g, 1 mmol) in 1,4-dioxane (1 ml). The solution was stirred at RT for 3 hours and added to water (30 ml). The white precipitate was collected and purified by precipitation from hot ethanol and water. Yield, 0.17 g (87%). $^1$H NMR (DMSO-d$_6$), (12.24 (s, 1H, NH), 8.14 (d, 1H, J=8.0 Hz, H-Ph), 8.10 (s, 4H, H-Ph), 8.02 (d, 1H, J=7.8 Hz, H-Ph), 7.83 (t, 1H, J=7.0 Hz, H-Ph), 7.56 (t, 1H, J=7.6 Hz, H-Ph), 2.00 (s, 3H, CH$_3$); EI MS m/z 349 (MH$^+$); Anal. Calcd (C$_{15}$H$_{12}$N$_2$O$_4$S$_2$): C, 51.71.; H, 3.47; N, 8.04. Found: C, 51.42, H, 3.57, N, 8.04.

The second method was used to synthesize compound 2B, compound 22 BITA, compound 31 BITA and compound 34 BITA (see Table 1). To a mixture of 2,2'-dithiodibenzoyl chloride (0.32 g, 0.93 mmol) in CCl$_4$ (10 ml) was added a solution of 2.5% w/v Cl$_2$ in CCl$_4$ (10 ml). The mixture was stirred until it cleared (1 h). After filtration, the filtrate was bubbled with N$_2$ for 1 h, and a solution of sulfacetamide (0.2 g, 0.93 mmol) in N,N-dimethylacetamide (DMA, 4 ml) was added. The mixture was stirred for 2 h, ethyl ether (20 ml) was added, and the precipitate was collected and purified with hot ethanol and water. Yield for compound 2B, 0.3 g (92%); the same ¹H NMR and EI MS as method A. Anal. Calcd ($C_{15}H_{12}N_2O_4S_2$): C, 51.71; H, 3.47; N, 8.04. Found: C, 51.34, H, 3.64, N, 7.96.

Synthesis Spaced Disulfide Benzamide/Benzoisothiazolone Chemotype, Exemplary Compounds 23D, 24D and 25D Exemplary means to synthesize compounds 23D (see Table 1)or N,N'-(2,2'-dithiodibenzoyl)-bis-4-(aminomethyl) benzene-sulfonanide, 24D, or N,N'-(2,2'-dithiodibenzoyl)-bis-4-(2-aminoethyl)benzene-sulfonamide, and 25D, or N,N'-(2,2'-dithiodibenzoyl)-bis-4-(glycinamido)benzene-sulfonamide (see Table 1) follows. These compounds were prepared, respectively, from 4-(aminomethyl) benzene-sulfonamide (Aldrich), 4-(2-aminoethyl) benzenesulfona-mide (Aldrich), and N-glycylsulfanilamide. The latter compound was prepared by first treating sulfanilamide with equimolar amounts of bromoacetyl bromide and pyridine in DMA and recovering the bromoacetylated derivative after adding the reaction mixture to excess 0.5 M HBr. The dried, crude product was recrystallized from ethanol and converted to N-glycylsulfanilamide via a standard Gabriel reaction (preparing the phthalimido derivative and cleaving with hydrazine hydrate). Procedures for compound 2D, outline above, were then followed.

Compound 23D: ¹H NMR (DMSO-$d_6$), (9.34 (t, 1H, J=6.1 Hz, NH), 7.85 (d, 2H, J=8.3 Hz, H-Ph), 7.79 (d, 1H, J=7.6 Hz, H-Ph), 7.70 (d, 1H, J=8.0 Hz, H-Ph), 7.59 (d, 2H, J=8.3 Hz, H-Ph), 7.51 (t, 1H, J=7.7 Hz, H-Ph), 7.37 (m, 3H, $NH_2$ and H-Ph), 4.61 (d, 2H, J=5.9 Hz, $CH_2$); EI MS m/z 643 (MH⁺); Anal. Calcd ($C_{28}H_{26}N_4O_6S_4$): C, 52.32; H, 4.08; N, 8.72. Found: C, 52.10, H, 4.25, N, 8.53.

Compound 24D: ¹H NMR (DMSO-$d_6$), (8.81 (t, 1H, J=5.2 Hz, NH), 7.81 (d, 2H, J=8.0 Hz, H-Ph), 7.66 (d, 1H, J=8.0 Hz, H-Ph), 7.61 (d, 1H, J=7.3 Hz, H-Ph), 7.54-7.46 (m, 3H, H-Ph), 7.34 (m, 3H, $NH_2$ and H-Ph), 3.58 (q, 2H, J=6.3 Hz, $CH_2$—N), 3.01 (t, 2H, J=7.1 Hz, $CH_2$-Ph); EI MS m/z 671 (MH⁺); Anal. Calcd ($C_{30}H_{30}N_4O_6S_4$): C, 53.71; H, 4.51; N, 8.35. Found: C, 53.43, H, 4.68, N, 8.33.

Compound 25D: ¹H NMR (DMSO-$d_6$), (10.53 (s, 1H, HN-Ph), 9.09 (t, 1H, J=5.8 Hz, HN—$CH_2$), 7.87-7.83 (m, 5H, H-Ph), 7.72 (d, 1H, J=7.1, H-Ph), 7.55 (t, 1H, J=7.0 Hz, H-Ph), 7.39 (t, 1H, J=7.6 Hz, H-Ph), 7.31 (s, 2H, $NH_2$), 4.18 (d, 2H, J=3.7 Hz, $CH_2$); EI MS m/z 729 (MH⁺); Anal. Calcd ($C_{30}H_{28}N_6O_8S_4(H_2O)$): C, 48.25; H, 4.05; N, 11.25. Found: C, 48.54, H, 4.12, N, 11.20.

Synthesis N-Terminally Modified Aminophenyl Sulfone Chemotype, Exemplary Compound 34D Exemplary means to synthesize compound 34D (see Table 1) or N,N'-(2,2'-dithio dibenzoyl)-bis-4-sulfanilyl-N-[(2-nitrobenzyl)sulfonyl)]aniline, follows. Compound 26 was made in a similar manner as compound 2D, starting with 3-aminophenyl sulfone and 2,2'-dithiodibenzoyl chloride. To a solution of compound 26 (1.5 g, 1.9 mmol) in DMA (30 ml) was added (dropwise) a solution of 2-nitro-toluenesulfonyl chloride (1.4 g, 5.9 mmol) in 1,4-dioxane (10 ml). The solution was stirred at RT overnight and then transferred to vigorously stirred ethyl ether (300 ml). After removing the ether phase, the viscous liquid was diluted with DMF (15 ml). The diluted solution was added to water (200 ml) with stirring. The white precipitate was collected and purified by precipitation twice from hot ethanol and ethyl ether. Yield compound 34D: 1.92 g (84%). ¹H NMR (DMSO-$d_6$), (11.01 (s, 1H, HN—$SO_2$), 10.74 (s, 1H, HN—CO), 8.10-7.29 (m, 16H, H-Ph), 5.11 (s, 2H, $CH_2$); EI MS m/z 1165 (MH⁺); Anal. Calcd ($C_{52}H_{40}N_6O_{14}S_6$): C, 53.60; H, 3.46; N, 7.21. Found: C, 53.49, H, 3.84, N, 7.13.

Synthesis 2,3-Haloalkanoamido Benzamido Chemotype, Exemplary Compound 37

Exemplary means to synthesize compound 37 (see Table 1) or N-[2-(3-chloro-propionamido) benzoyl]sulfacetamide, follows. N-(2-nitrobenzoyl) sulfacetamide was made in a similar manner as 2D, but starting with 2-nitrobenzoyl chloride. One gram (2.7 mmol) of this product was dissolved in methanol (100 ml) at 45° C. The solution was cooled to room temp. and then bubbled with $N_2$ to remove air. To the solution was added palladium, 10 wt. % on activated carbon, (0.22 g) under $N_2$. The mixture was bubbled with $H_2$ for 1.5 h and then with $N_2$ for 0.5 h. After filtration, the filtrate was evaporated to dryness. Yield, 0.84 g (93%) of white-yellow product. This 2-aminobenzamido derivative was reacted with 3-chloropropionyl chloride under conditions similar to those described for compound 34D, yielding compound 37. ¹H NMR (DMSO-$d_6$), (12.06 (s, 1H, NH—$SO_2$), 10.84 (s, 1H, NH-Ph), 10.32 (s, 1H, NH-Ph), 8.03-7:91 (m, 5H, H-Ph), 7.76 (d, 1H, J=7.7 Hz, H-Ph), 7.60 (t, 1H, J=7.8 Hz, H-Ph), 7.32 (t, 1H, J=7.6 Hz, H-Ph), 3.87 (t, 2H, J=6.1 Hz, $CH_2Cl$), 2.86 (t, 2H, J=6.2 Hz, $CH_2$), 2.00 (s, 3H, $CH_3$); EI MS m/z 424 (MH⁺); Anal. Calcd ($C_{18}H_{18}N_3O_5SCl$): C, 51.00; H, 4.28; N, 9.91. Found: C, 50.85, H, 4.49, N, 9.96.

Synthesis Haloalkanoyl Thioester Chemotype, Exemplary Compound 44

Exemplary means to synthesize compound 44 (see Table 1) or N-[2-(5-bromovaleroylthio) benzoyl]sulfacetamide, follows. N-(2-mercaptobenzoylsulfacetamide was first prepared by adding to a solution of 2D (2.2 g, 3.1 mmol) in 90% DMF (20 ml), tris(2-carboxyethylphosphine hydrochloride (1 g, 3.5 mmol) and triethylamine (0.5 ml). The solution was stirred for 1 h and then added to 0.5 M HCl (200 ml). The precipitate was collected and dried, yielding 2.3 g (95%). To a solution of this product (0.5 g, 1.4 mmol) in DMA (5 ml) was added 5-bromovaleryl chloride (0.6 ml, ~4.5 mmol) under $N_2$. The solution was stirred under $N_2$ for 1 h and added to ethyl ether (50 ml). After decanting the ether phase, the remaining viscous liquid was dissolved in DMF (10 ml). The solution was added to vigorously stirred water (100 ml). The white precipitate was filtered off and purified from hot ethanol and water. Yield compound 44: 0.47 g (65%). ¹H NMR (DMSO-$d_6$), (12.05 (s, 1H, $HNSO_2$), 10.91 (s, 1H, HN-Ph), 7.94 (s, 4H, H-Ph), 7.74-7.61 (m, 4H, H-Ph), 3.48 (t, 2H, J=6.3 Hz, $CH_2Br$), 2.74 (t, 2H, J=7.1 Hz, $CH_2CO$), 1.96 (s, 3H, $CH_3$), 1.90-1.64 (m, 4H, $CH_2CH_2$); EI MS m/z 515 (MH⁺); Anal. Calcd ($C_{20}H_{21}N_2O_2S_2Br$): C, 46.79; H, 4.12; N, 5.46. Found: C, 47.16, H, 4.31, N, 5.60.

Synthesis of Pyridinioalkanoyl Thioester Chemotype, Exemplary Compound 45

Exemplary means to synthesize compound 45 (see Table 1) or N-[2-(5-pyridinio-valeroylthio) benzoyl]sulfacetamide bromide, follows. A solution of compound 44 (0.25 g, 0.49 mmol) in pyridine (7 ml) was stirred under $N_2$ overnight. Ethyl ether (80 ml) was added, and the white precipitate was collected and purified from hot ethanol and ether; the precipitate was dried in vacuum immediately. Yield compound 45, 0.21 g (72%). ¹H NMR (DMSO-$d_4$), (12.10 (br. s, 1H, $HNSO_2$),10.94 (s, 1H, HN-Ph), 9.12 (d, 2H, J=6.1 Hz, 2,6-H-Py), 8.65 (t, 1H, J=7.2 Hz, 4-H-Py), 8.21 (t, 2H, J=7.0 Hz, 3,5-H-Py), 7.94 (S, 4H, H-Ph), 7.74-7.58 (m, 4H, H-Ph), 4.62 (t, 2H, J=7.2 Hz, $CH_2$-Py), 2.79 (t, 2H, J=7.2 Hz, $CH_2$—CO), 1.92 (m, 5H, $CH_3$ and $CH_2$), 1.57 (pentet, 2H, J=7.6 Hz, $CH_2$); EI MS m/z 512 (M⁺); Anal. Calcd ($C_{25}H_{26}N_3O_5S_2Br$): C, 50.68; H, 4.42; N, 7.09. Found: C, 50.54, H, 4.68, N, 7.22.

Synthesis of Thiolesters Represented by Templates I, II and III

Exemplary means to synthesize the thiolester compounds represented by Templates I, II and III follow. As discussed above, the skilled artisan can use any synthetic scheme or any variation to an exemplary protocol to generate a thiolester of the invention.

In templates II and IIIb, where X is —$CH_2$—, —$CH_2CH_2$— and —$CH_2C$(═O)—NH—, the thiolester can be generated using methods for synthesizing compounds 23D, 24D and 25D, respectively, described above (see Table 1).

Where the thiolester is N-[2-(α-Pyridinio-4-toluoylthio) benzoyl] sulfacetamide chloride, a solution of N-(2-mercaptobenzoyl) sulfacetamide (see synthesis compound 44) (0.4 g) and 4-(chloromethyl) benzoyl chloride (0.6 ml) in dimethylacetamide (2 ml) was stirred under nitrogen for 1 h, and then added to ethyl ether (40 ml) with stirring. The viscous liquid precipitate was diluted with dimethylformamide (1 ml), and then added to a solution of ether (40 ml) and heptane (40 ml). The viscous liquid precipitate was collected and added to pyridine (3 ml). The solution was stirred at RT under Ar for 3 days, and then added to ether (50 ml). The precipitate was collected and dried. The crude product was purified on a silica gel column using isocratic elution with 10% AcOH in MeOH.

Where the thiolester is N-[2-(2-(Pyridinioacetamido)benzoylthio) benzoyl]sulfacetamide chloride, an analog of compound 37 was prepared in the same manner except that chloroacetyl chloride was substituted for 3-chloropropionyl chloride. This product was dissolved in pyridine and allowed to stand at RT, and the product was worked up as described above for N-[2-(α-Pyridinio-4-toluoylthio)benzoyl] sulfacetamide chloride.

Where the thiolester is N-[2-(Pyridinio acetamido acetylthio)benzoyl] sulfacetamide chloride, N-(2-Mercaptobenzoyl)sulfacetamide is prepared as described for compound 44. Chloroacetylglycine may be linked to the thiol group of this product following activation of the glycine carbonyl group via (a) a p-nitrophenyl ester derivative, or (b) an acid chloride prepared using oxalyl chloride. Workup and subsequent reaction with pyridine is carried out as described for N-[2-(α-Pyridinio-4-toluoylthio) benzoyl]sulfacetamide chloride, described above.

Where the thiolester is N-[2-(2-(Pyridinioacetamido) isobutyrylthio) benzoyl]sulfacetamide chloride, the compound can be prepared in a similar manner as is N-[2-(Pyridinio acetamido acetylthio)benzoyl]sulfacetamide chloride, described above, except that N-chloroacetyl-2-aminoisobutyric acid (prepared according to Birnbaum (1952) *J. Biol. Chem.* 194:455 and Ronwin (1953) *J. Org. Chem.* 18:127,) is substituted for chloro-acetylglycine.

Where the thiolester is N-[2-(5-Dimethylsulfoniovaleroylthio) benzoyl]sulfacetamide iodide, wherein Z═—$S^+$($CH_3$)$_2$ and Y═—($CH_2$)$_4$—: a mixture of compound 44 (1.10 g) and NaI (5 g) in acetone (99.9%, 25 ml) was stirred under nitrogen at RT overnight, and then added to water (250 ml) with stirring. The white precipitate was collected and dried. Yield, 1.2 g. A clear solution of this product (0.3 g) in acetonitrile (3 ml) and methyl sulfide (4 ml) was stirred at RT overnight. The clear solution was added to ethyl ether (250 ml) with vigorous stirring. The white precipitate was collected, washed with ether, and dried. Yield, 0.15 g.

Where the thiolester is N-[2-(5-Triethyl ammoniovaleroylthio) benzoyl] sulfacetamide iodide, wherein Z═—$N^+$($C_2H_5$)$_3$ and Y═—($CH_2$)$_4$—: a parallel synthesis to N-[2-(5-Dimethylsulfoniovaleroylthio)benzoyl]sulfacetamide iodide may be conducted wherein triethylamine is substituted for methyl sulfide. Refluxing may be required to finish reaction with triethylamine.

Where the thiolester is N-[2-(5-Tri-n-butylphosphonio valeroylthio) benzoyl]sulfacetamide iodide, wherein Z═—$P^+$($C_4H_9$)$_3$ and Y═—($CH_2$)$_4$—: a parallel synthesis to N-[2-(5-Dimethylsulfoniovaleroylthio) benzoyl]sulfacetamide iodide may be conducted wherein tri-n-butylphosphine is substituted for methyl sulfide.

To synthesize a thiolester specie of Template III, where G is t-butyl, Y is —$CH_2$—, X is —$CH_2$—, the pyridine ring bears a substituted carboxamide group at $R_8$ and $R_{10}$, $R_6$ is H, $R_9$ is ═—$SO_2$—$NH_2$, and $R_7$, $R_8$, $R_{10}$, $R_{11}$ is H: 4-[1-(t-Butylthiocarbonylmethyl) nicotinamidomethyl]-benzenesulfonamide chloride triethylamine (36 mmol) and nicotinoyl chloride hydrochloride (30 mmol) were added to a suspension of 4-(aminomethyl) benzenesulfonamide hydrochloride hydrate (30 mmol) in 150 ml acetonitrile. An additional 60 mmol of triethylamine were added gradually. The precipitate of 4-(nicotinamidomethyl) benzenesulfonamide was recrystallized from a solution of 12 ml ethanol in 180 ml water. Product dried in vacuo/$CaCl_2$. Next, S-chloroacetyl-t-butyl mercaptan is prepared by reacting chloroacetyl chloride and t-butyl mercaptan according to Dawson (1947) *J. Amer. Chem. Soc.* 69:1211. The thiolester is generated by stirring 10 mmol of the nicotinamide derivative with 20 mmol of the chloroacetyl thioester in 125 ml acetonitrile at reflux overnight. On standing at RT, the product crystallizes out. It may be recrystallized from an ethanol-water mixture.

In templates II and IIIb, where $R_1$ is alkyl, —$CH_3$, —($CH_2$) n-$CH_3$, —$CH(CH_3)_2$, —$C(CH_3)_3$, -aryl, -arylalkyl, -Ph-$CH_3$, arylalkoxy, -Ph-$OCH_3$, nitroaryl, -Ph-$NO_2$, —($CH_2$)$_n$—X where X is a halogen, —($CH_2$)$_n$—Cl, —($CH_2$)$_n$—Br, or —($CH_2$)$_n$—I; the group of N-(2-acylthiobenzoyl)sulfacetamides, having acyl groups with the formula $R_1$—C(═O)— and $R_1$'s taken from these alternative $R_1$ structures, can be prepared as described for compound 44 and substituting $R_1$—C(═O)—Cl for 5-bromovaleryl chloride.

Thiolesters based on Templates I and II with R2 being —$CH_3$ rather than H, can be prepared in the same manner as compounds 44 and 45 by substituting 2,2'-dithiobis (3-methylbenzoyl chloride) for 2,2'-dithiodi-benzoyl chloride in the preparation of the precursor, compound 2D. The 3-methyl derivative can be prepared according to the method of Collman and Groh (1982) *J. Amer. Chem. Soc.* 104:1391-1400.

Thiolesters based on Template I with R6 being —CH3 can be prepared as described for compounds 44 and 45, except that, in place of sulfacetamide, N-methyl-4-(4-nitrobenzenesulfonyl)aniline is used and prepared as described by Saxena (1989) *Arzneim. Forsch.* 39:1081-1084.

Thiolesters based on Template II with $R_6$ being —$CH_3$ can be prepared as described for compounds 44 and 45, except that 2-methylamino-N-(4-sulfamoylphenyl) acetamide is used and the thiolester prepared according to Horstmann (1977) *Eur. J. Med. Chem. Chim. Ther.* 12:387-391.

Thiolesters based on Template II with R6 being aryl or phenyl can be prepared as described for compounds 44 and 45, except that, in place of sulfacetamide, one would use N-phenylglycyl-sulfanilic acid amide, prepared as described by Gaind, Sehgal and Ray; J. (1941) *Indian Chem. Soc.* 18:209.

Design and Synthesis of Thiolesters Capable of Dissociating Metal Ions from Zinc Fingers Viral zinc fingers, particularly the zinc finger in the nucleocapsid protein of NCp7 of HIV-1, are used as models to design the novel thiolesters of the invention. NCp7 possess regions on their solvent accessible surfaces where favorable interactions with candidate ligands may occur. Each zinc finger has two potential high affinity binding sites. One comprises the putative mRNA binding site near Phe17 on finger 1 and Trp37 on finger 2. The other site is near the metal coordinating histidine in each finger, opposite the putative mRNA site. For the purposes of designing novel thiolesters capable of dissociating metal ions from zinc fingers, the ligand binding site opposite the putative mRNA binding region was considered the stronger of the two candidate binding sites. These binding regions were probed with a range of possible hydrophobic and hydrophilic atom types. Those types with the strongest possible binding interactions were selected.

Further modeling studies of the interactions of ligands (agents) with NCp7 suggested that both disulfide benzamides (DIBAs) and benzoisothiazolone derivatives (BITAs) can interact with hydrophobic patches on the surfaces of both retroviral Zn fingers in such a way as to orient the reactive groups of these agents into close proximity with the nucleophilic cysteine sulfur atoms in each finger. In contrast, DIBAs failed to interact with the cysteine sulfur atoms in the Zn fingers of the transcriptional factor GATA-1 due to steric exclusion (Huang (1998) *J. Med. Chem.* 41:1371-1381). Disulfides and their respective BITA derivatives were designed, synthesized and purified, and the antiviral and in vitro NCp7 zinc ejection activities were assessed.

TABLE 1

Synthesis of Novel Disulfides and Benzoisothiazolone Forms Derived From the DIBA-1 and DIBA-2 Chemotypes

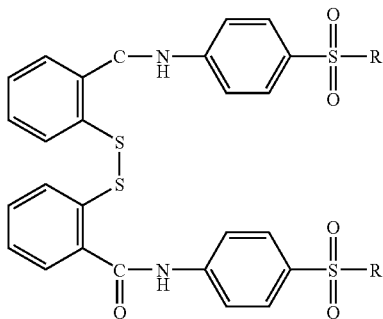

Dimer (D Form)

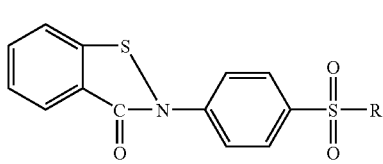

Benzoisothiazolone (BITA Form)

| | | | | Antiviral Activity[a] | | |
|---|---|---|---|---|---|---|
| Compound | R | | Form | $EC_{50}$ μM | $IC_{50}$ μM | TI |
| 1 | —$NH_2$[b] | | D | 0.85 | 217 | 255.3 |
| | | | BITA | — | 16.2 | |
| 2. | —NH—C(=O)—$CH_3$[c] | | D | 1.5 | >200 | >133 |
| | | | BITA | 12.6 | 34 | 2.7 |
| 3. | —NH—C(=O)—phenyl | | D | 3.8 | 54.1 | 14.2 |
| | | | BITA | 9.3 | 49.5 | 5.3 |
| 4. | —NH—(6-chloropyridazin-3-yl) | | D | 2.9 | 18.3 | 6.3 |
| | | | BITA | 7.1 | 19.2 | 2.7 |
| 5. | —NH—(pyrimidin-2-yl) | | D | 2 | 46.4 | 23.2 |
| | | | BITA | 6.5 | 50.8 | 7.8 |

TABLE 1-continued
Synthesis of Novel Disulfides and Benzoisothiazolone Forms
Derived From the DIBA-1 and DIBA-2 Chemotypes
[Dimer (D Form)]
[Benzoisothiazolone (BITA Form)]
| Compound | R | Form | Antiviral Activity[a] | | |
|---|---|---|---|---|---|
| | | | EC$_{50}$ μM | IC$_{50}$ μM | TI |
| 6. | 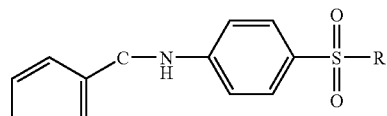 | D<br>BITA | 2.1<br>7.6 | 52.5<br>56.6 | 25<br>7.4 |
| 7. | 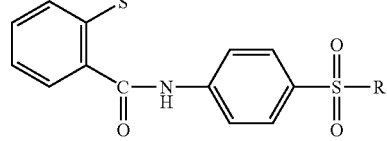 | D<br>BITA | 4.2<br>8.8 | 56.7<br>57.4 | 13.5<br>6.5 |
| 8. | | D<br>BITA | 2.1<br>17.8 | 55.5<br>57.6 | 26.2<br>3.3 |
| 9. | 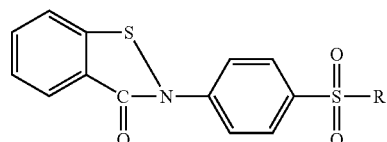 | D<br>BITA | 1.6<br>6.9 | 32.2<br>17.1 | 20.1<br>2.5 |
| 10. | | D<br>BITA | 3.4<br>7.8 | 18.6<br>17.3 | 5.5<br>2.2 |
| 11. | | D<br>BITA | 1.9<br>8.7 | 27.6<br>54.6 | 14.5<br>6.3 |

TABLE 1-continued

Synthesis of Novel Disulfides and Benzoisothiazolone Forms
Derived From the DIBA-1 and DIBA-2 Chemotypes

[Dimer (D Form) structure]

[Benzoisothiazolone (BITA Form) structure]

| Compound | R | Form | Antiviral Activity[a] | | |
|---|---|---|---|---|---|
| | | | EC$_{50}$ μM | IC$_{50}$ μM | TI |
| 12. | 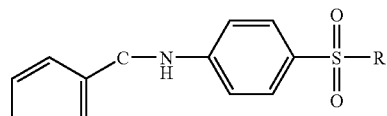 —NH—(pyridazine)—OCH$_3$ | D<br>BITA | 4.2<br>22.6 | 53.8<br>55.3 | 12.8<br>2.4 |
| 13. | —NH—(pyrimidine)—OCH$_3$ | D<br>BITA | 1.6<br>NT[d] | 46.5 | 29.1 |
| 14. | 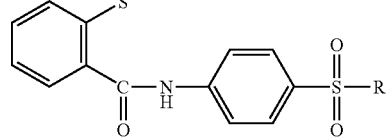 —NH—(oxazole with CH$_3$, CH$_3$) | D<br>BITA | 2.4<br>NT | 46.4 | 19.3 |
| 15. | 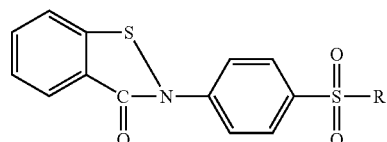 —NH—(phenyl-pyrazole) | D<br>BITA | 0.33<br>NT | 19.5 | 59.1 |
| 16. | —NH—(pyridine) | D<br>BITA | 1.1<br>NT | 17.8 | 16.2 |
| 17. | —NH—(quinoxaline) | D<br>BITA | 0.72<br>9.2 | 22.2<br>54.7 | 30.8<br>5.9 |

TABLE 1-continued

Synthesis of Novel Disulfides and Benzoisothiazolone Forms Derived From the DIBA-1 and DIBA-2 Chemotypes

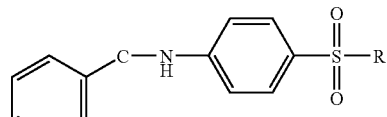

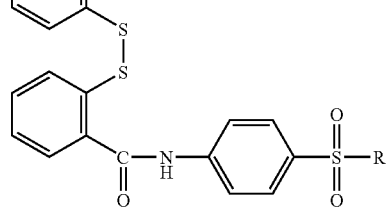

Dimer (D Form)

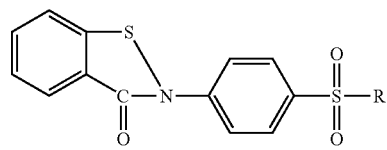

Benzoisothiazolone (BITA Form)

| Compound | R | Form | Antiviral Activity[a] $EC_{50}$ μM | $IC_{50}$ μM | TI |
|---|---|---|---|---|---|
| 18. | (2-aminothiazole) | D | 1 | 18 | 18 |
|  |  | BITA | NT |  |  |
| 19. | (2,6-dimethylpyrimidin-4-ylamino) | D | 1.9 | 18.2 | 9.6 |
|  |  | BITA | 6.5 | 39.7 | 6.1 |
| 20. | (3,4-dimethylisoxazol-5-ylamino) | D | 2.5 | 44.2 | 17.7 |
|  |  | BITA | 12.8 | 39.0 | 3.0 |
| 21. | (guanidino) | D | 111 | >316 | >2.8 |
|  |  | BITA | NT |  |  |
| 22. | (4-sulfamoylphenylamino) | D | 2.3 | 43 | 18.7 |
|  |  | BITA | 6.2 | 18.1 | 2.9 |

[a]Antiviral activity was measured in the XTT cytoprotection assay.
[b]Originally reported as DIBA-1
[c]Originally reported as DIBA-2
[d]NT designates compounds that could not be made in sufficient quantity and or purity to analyze

TABLE 2

Modification of the DIBA-2 Chemotype by Backbone Linker Substitutions

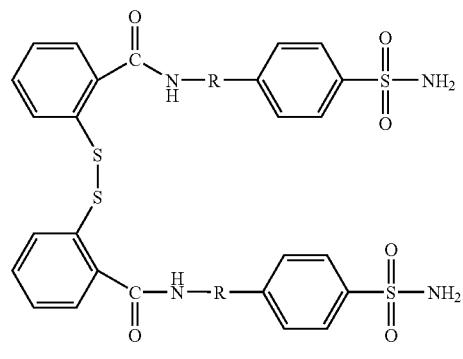

Disulfide (D Form)

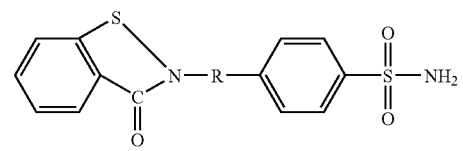

Benzoisothiazolone (BITA Form)

| Compound | R | Form | Antiviral Activity[a] | | | Zinc Finger Reactivity |
|---|---|---|---|---|---|---|
| | | | $EC_{50}\,\mu M$ | $IC_{50}\,\mu M$ | TI | RFU/30 min[b] |
| 23. | —CH$_2$— | D | 0.33 | 19.4 | 58.8 | 3.3 |
| | | BITA | 13.8 | 53.7 | 3.9 | 2.7 |
| 24. | —(CH$_2$)$_2$— | D | 0.41 | 52.8 | 139 | 2.7 |
| | | BITA | 2 | 45.5 | 22.7 | 2.7 |
| 25. | —CH$_2$—C(O)—NH— | D | 1.6 | 17.6 | 11 | 7.9 |

[a]Antiviral activity was measured by the XTT cytoprotection assay

[b]Zinc finger reactivity measured by the Trp37 fluorescence assay. Results are expressed as the average decrease in relative TABLE 3
Optimization of the Bis(Aminophenyl)Sulfone-Based Disulfide Benzamides
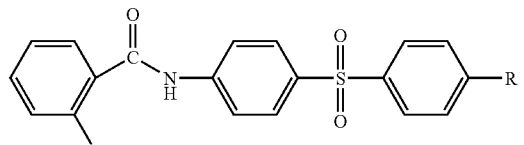
Disulfide (D Form)
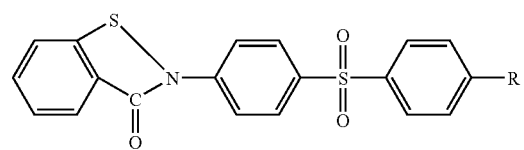
Benzoisothiazolone (BITA Form)
| Compound | R | Form | Antiviral Activity[a] EC$_{50}$ μM | IC$_{50}$ μM | TI | Zinc Finger Reactivity RFU/min[b] |
|---|---|---|---|---|---|---|
| 26. | —NH$_2$ | D | 4.3 | <316 | >73.5 | 3.3 |
| 27. | —NH—C(=O)—CH$_3$ | D | 1.5 | 160 | 106.7 | 5.9 |
| 28. | —NH—SO$_2$—C$_6$H$_4$—NH—C(=O)—CH$_3$ | D | 1.0 | 12.7 | 12.7 | 5.9 |
|  |  | BITA | 9.6 | 188 | 19.6 | 7.9 |
| 29. | —NH—C(=O)—C$_6$H$_4$—OCH$_3$ | D | 3.8 | 79.6 | 20.9 | 6.9 |
| 30. | —NH—C(=O)-(2-thienyl) | D | 12.2 | 190 | 15.6 | — |
| 31 | —NO$_2$ | D | 12.2 | >316 | >26 | 2.9 |
|  |  | BITA | — | >316 | — | 4.1 |

TABLE 3-continued

Optimization of the Bis(Aminophenyl)Sulfone-Based Disulfide Benzamides

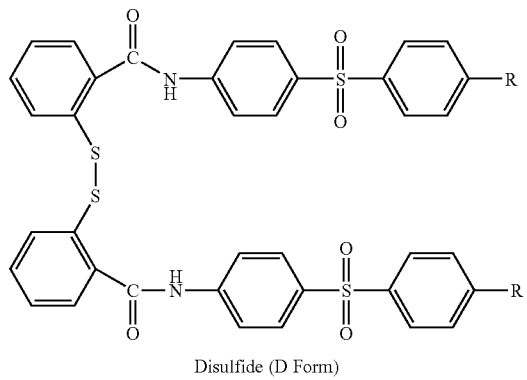

Disulfide (D Form)

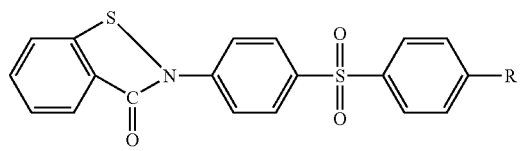

Benzoisothiazolone (BITA Form)

| Compound | R | Form | Antiviral Activity[a] | | | Zinc Finger Reactivity |
| | | | $EC_{50}$ μM | $IC_{50}$ μM | TI | RFU/min[b] |
| --- | --- | --- | --- | --- | --- | --- |
| 32. | —NH—C(O)—C6H4—NO2 | D | 78 | >316 | >4 | 2.9 |
| 33. | —NH—C(O)—C6H3(NO2)2 (3,5) | D | 240 | >316 | >1.3 | 1.6 |
| 34 | —NH—S(O)2—CH2—C6H4—NO2 (2) | D | 12.3 | >316 | >25.7 | 1.5 |
| | | BITA | 3.2 | 59.5 | 15.1 | 2 |

[a] Antiviral activity was measured by the XTT cytoprotection assay
[b] Zinc finger reactivity was measured by the Trp37 fluorescence assay. Results are expressed as the average decrease in relative

TABLE 4

3,3' Bis(Aminophenyl) Sulfone Isomers

| Reactivity Compound | R | Antiviral Activity[a] EC$_{50}$ μM | IC$_{50}$ μM | TI | Zinc Finger RFU/min[b] |
|---|---|---|---|---|---|
| 35 | —NH$_2$ | 1 | 81.5 | 81.5 | 0.92 |
| 36. | —NH—C(=O)—CH$_3$ | 0.62 | 5.9 | 95 | 2 |

[a]Antiviral activity was measured by the XTT cytoprotection assay
[b]Zinc Finger reactivity measured by the Trp37 fluorescence assay. Results are expressed as the average decrease in relative fluorescence units over 30 min.

TABLE 5

Single Liganded (Monomer) Benzamides Linked to Haloalkanoyl Groups via Amide or thioester Bonds

| Reactivity Compound | R1 | R2 | Antiviral Activity[a] EC$_{50}$ μM | IC$_{50}$ % | TI | Zinc Finger Reactivity RFU/min[b] |
|---|---|---|---|---|---|---|
| | | Amide: | | | | |
| 37. | —NH—C(=O)—(CH$_2$)$_2$—Cl | H | — | >316 | — | 2.0 |
| 38 | H | —NH—C(=O)—(CH$_2$)$_2$—Cl | 38 | 103 | 2.8 | 3.9 |
| 39. | —NH—C(=O)—CH$_2$—Cl | H | — | 202 | — | 0.3 |

TABLE 5-continued

Single Liganded (Monomer) Benzamides Linked to Haloalkanoyl Groups via Amide or thioester Bonds

| Reactivity Compound | R1 | R2 | Antiviral Activity[a] EC$_{50}$ μM | IC$_{50}$ % | TI | Zinc Finger Reactivity RFU/min[b] |
|---|---|---|---|---|---|---|
| | | Thioesters: | | | | |
| 40. | —S—C(=O)—CH$_3$ | H | 2.8 | 56.7 | 20.3 | 4.2 |
| 41. | —S—C(=O)—C$_6$H$_5$ | H | 2.6 | 45.7 | 16.6 | 2.2 |
| 42. | —S—C(=O)—C$_6$H$_4$—OCH$_3$ | H | 2.8 | 43.7 | 15.6 | 3.5 |
| 43. | —S—C(=O)—C$_6$H$_4$—(CH$_2$)$_2$—Cl | H | 4.2 | 62 | 14.8 | 9.2 |
| 44. | —S—C(=O)—(CH$_2$)$_4$—Br | H | 3.8 | 184.5 | 49.2 | 1.8 |
| 45. | —S—C(=O)—(CH$_2$)$_4$—$^+$N-pyridinium Br$^-$ | H | 6.2 | >316 | >51 | 3.6 |

[a]Antiviral Activity was measured by the XTT cytoprotection assay
[b]Zinc finger reactivity measured by the Trp37 fluorescence assay. Results are expressed as the average decrease in relative fluorescence units over 30 min.

TABLE 6

Evaluation of Pyridinoalkanoyl thioesters (PATEs) and 4-bromovaleroyl Thioesters R1: —S—C(=O)—(CH$_2$)$_4$—Br R2: —S—C(=O)—(CH$_2$)$_4$—$^+$N(pyridine) Br$^-$

| Compound | R Group | Antiviral Activity$^a$ EC$_{50}$ %μM | IC$_{50}$ μM | TI | Zinc Finger Reactivity RFU/min$^b$ |
|---|---|---|---|---|---|
| | | Compound 2 Backbone: | | | |
| 44. | R1 | 38 | 184.5 | 49.2 | 1.8 |
| 45. | R2 | 6.2 | >316 | >51 | 3.6 |
| | | Compound 31 Backbone: | | | |
| 46. | R1 | 1.6 | 21.7 | 13.6 | 1 |
| 47. | R2 | 5.5 | >316 | >57 | 4.1 |
| | | Compound 23 Backbone: | | | |
| 48. | R2 | 1.1 | 55 | 50 | 1.4 |
| | | Compound 34 Backbone: | | | |
| 49. | R1 | — | >316 | — | 1.9 |
| 50. | R2 | 2.9 | >316 | >109 | 0.86 |
| | | Compound 27 Backbone: | | | |
| 51. | R2 | 4.6 | 288 | 63 | 1.7 |
| | | Compound 36 Backbone: | | | |
| 52. | R2 | 4.9 | 205 | 43 | 1.1 |
| | | Partial Structure (R2): HO—C(=O)—(CH$_2$)$_4$—$^+$N(pyridine) Br$^-$ | | | |
| 53. | — | — | >316 | | 4 |

$^a$Antiviral Activity was measured by the XTT cytoprotection assay
$^b$Zinc finger reactivity measured by the Trp37 fluorescence assay. Results are expressed as the average decrease in relative fluorescence units over 30 min.

TABLE 7

Antiviral Mechanism of Action

| Activity$^b$ | Compound (I$_{50}$:M$^a$) 44 | 45 | 47 |
|---|---|---|---|
| Integrase | NI$^c$ | NI | NI |
| Reverse transcriptase | | | |
| rAdT | NI | NI | NI |
| rCdG | NI | NI | NI |
| Protease | NI | NI | NI |
| Zinc Finger Reactivity$^d$ | 1.8(13.3%) | 3.6(34.7%) | 4.1(17.9%) |
| Attachment | NI | NI | NI |
| Fusion | >100 | 77 | 99 |

$^a$I50 Concentration of compound inhibiting 50% of the indicated activity.
$^b$All positive controls for individual assays are as noted in the Experimental Section.
$^c$No inhibition (NI) at a high dose test of 100 μM.
$^d$Expressed as decrease in relative fluorescence units per 30 min. (RFU/30 MIN), with percent total decrease in flourescence given in parenthesis.

TABLE 8

Effect of glutathione on Antiviral Activity of Selected PATEs and 5-Bromovaleroyl Thioesters

| Compound | GSH[b] | Zinc Finger Reactivity[a] RFU/min | % Decrease |
|---|---|---|---|
| 44 | − | 6.5 | 60.1 |
|  | + | 2.4 | 28 |
| 45 | − | 2.6 | 28.2 |
|  | + | 3.8 | 36.9 |
| 47 | − | 1.6 | 24.3 |
|  | + | 1.6 | 21.1 |
| PBS control | − | 0 | 0 |
|  | + | 1.3 | 7.9 |

[a]Zn ringer reactivity was measured by the Trp37 flourescence assay. Reactivity is expressed as either the average change in fluorescence units per 30 min (RFU/min) or as the total percent decrease during a 30 min incubation (% decrease).
[b]Compounds (2 mM) were treated for 2 h at 37° C. with 4 mM reduced glutathione. Following incubation reactions were diluted to a final concentration of μM and activity in the Trp37 Zn ejection determined as previously described.

TABLE 9

Summary of Zinc Finger Reactivity for Compounds 44, 45 and 47

| Compound | NCp7 (Trp37) | Virion Cross-link | Nucleic Acid Binding ($I_{50}$ μM) | Virucidal Activity ($I_{50}$ μM) | U1 Inhibition of p24 ($EC_{50}$ μM) | Gag Precursor Cross-linking |
|---|---|---|---|---|---|---|
| 44 | + | −/+ | 100 | 12.3 | 94 | +/− |
| 45 | + | +++ | 1 | 13.2 | 42.2 | +/− |
| 47 | + | −/+ | 100 | 2.1 | 10.7 | +++ |

TABLE 10

Evaluation of Structural Features Comprising the Pyridinoalkanoyl Side Chain of the PATEs

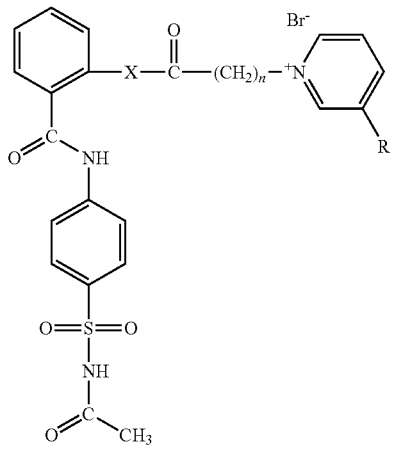

| Compound | X | n | R | Antiviral Activity[b] $EC_{50}$ % μM | $IC_{50}$ % | TI | Zinc Finger Reactivity RFU/min[b] |
|---|---|---|---|---|---|---|---|
| 54 | S | 3 | H | 10.1 | 175 | 17.3 | 2.2 |
| 45 (parental PATE) | S | 4 | H | 6.2 | >316 | >51 | 3.6 |
| 55 | S | 5 | H | 10.5 | 69.7 | 6.5 | 1.9 |
| 56 | NH | 4 | H | — | >316 | — | 2.6 |
| 57 | S | 4 | Cl | 54 | 264 | 4.8 | 0.2 |

[a]Antiviral Activity was measured by the XTT cytoprotection assay
[b]Zinc finger reactivity measured by the Trp37 fluorescence assay. Results are expressed as the average decrease in relative fluorescence units over 30 min.

Disulfide, and where synthetically possible, the BITA forms, of compounds 1 through 36 were synthesized (Tables 1 to 4) and their antiviral activity was assessed in the XTT cytoprotection assay (described below).

Essentially all compounds generated for these studies possessed some degree of antiviral activity (XTT cytoprotection assay) and zinc finger reactivity. Zinc finger reactivity was measured using a Zn specific fluorochrome, TSQ, N-(6-methoxy-8-quinolyl)-p-toluenesulfonamide, assay or a Trp37 zinc finger fluorescence assay. Fluorescent measurements of the Trp37 residue in the C-terminal finger of recombinant HIV-1 NCp7 protein were performed as described by Rice (1995) *Science* 270:1194-1197; Rice (1997) *Antimicrob. Agents Chemother.* 41:419-426. Measurement of Zn ejection from both fingers was measured using the Zn-selective fluorchrome probe TSQ (Molecular Probes, Eugene Oreg.) as described by Rice (1996) *J. Med. Chem* 39:3606-3616. Measurement of the ability of NCp7 to bind to a DNA oligomer, a 44 mer: GGC GAC TGG TGA GTA CGC CAA AAA TTT TGA CTA GCG GAG GCT AG (SEQ ID NO:1), analogous to the HIV-1 RNA packaging site was carried out as described by Huang (1998) *J. Med. Chem.* 41:1371-1381, see also, Rossio (1998) HIV Pathogenesis and Treatment: Keystone Symposium on Molecular and Cellular Biology, Abstract # 4082. Briefly, 50 nM NCp7 was treated with test compounds for 1 hour at RT in 10 ml buffer containing 10% glycerol and 50 mM Tris-HCl (pH 7.5). Labeled oligomer (0.1 picomole, end labeled [$^{32}$P] was added in an equal volume of buffer containing 10% glycerol, 50 mM Tris-HCl (pH 7.5), 400 mM KCl and 40 mM $MgCl_2$. The reaction was continued for 15 min at room temperature, and a total of 5 ml (or ¼ of the total reaction volume) was separated on nondenaturing 4.5% polyacrylamide gels in 0.5× Tris-Borate electrophoresis buffer. NCp7-oligomer complexes were visualized by autoradiography.

Among the new disulfide-based analogs, compounds 26, 31 and 34 exhibited no toxicity at the high test dose of 316 µM (micromolar) and exhibited an $EC_{50}$ (concentration inhibiting 50% virus replication) of 4.3, 12.2 and 12.3 µM, respectively. The aminophenyl substitution used to generate compound 26 converted the ligand portion of the DIBA into a bis (4-aminophenyl) sulfone. N-acetylation of compound 26 yielded compound 27 with a lower $EC_{50}$ (1.5 µM) but with greater toxicity (160 µM). Conversion of the bis(aminophenyl) sulfone bridge of compound 26 to a sulfonamido group and changing the terminal amine to a primary sulfonamide (compound 22, Table 1) resulted in much greater cellular toxicity (43 µM). Generally, where disulfide/BITA pairs could be synthesized, there was an average of a 4-fold (n=15, range 1.5- to 8-fold) drop in the in vitro therapeutic index ($IC_{50}/EC_{50}$), primarily because of a loss in antiviral potency, i.e., increased $EC_{50}$ values. There was not an enhanced cellular toxicity. None of the new disulfides or BITAs were superior to compound 1.

Molecular modeling suggested that better fits of agents onto the NCp7 Zn finger atomic surface binding domains could be achieved by the addition of methylene (compound 23) or ethylene (compound 24) spacers in the backbones between the benzamido head group and the benzenesulfonamide ligand group of compound 1 (Table 2). Antiviral activity and Zn finger reactivity were maintained, but these modifications were associated with a 4- to 10-fold decrease in $IC_{50}$ (more cytotoxic) when compared to the parental compound 1. As seen in Table 2, the corresponding BITAs demonstrated a significant loss of antiviral activity (compound 23: 42-fold decrease, and compound 24: 5-fold decrease), even though reactivity against purified NCp7 was maintained. Further modification of the head group spacer by addition of a carbamyl group to compound 23 (see compound 25) enhanced zinc finger reactivity (RFU/min 7.9 versus 3.3), but decreased antiviral potency.

Optimization of Bis(aminophenyl) Sulfone-Based Disulfide Benzamides

Incorporation of 4,4'-bis(aminophenyl) sulfone onto the disulfide head group yielded compound 26 with a terminal amine as a synthetic locus for further modifications. Several acyl modifications generated compounds 27, 28 and 29, which resulted in increased zinc finger reactivity and improved $EC_{50}$. These gains were partially (compounds 27 and 29) and completely (compound 28) offset by decreases in the $IC_{50}$. Thus far, terminal extension of the ligand portion of 26 did not yield a significantly improved antiviral agent.

The BITA derivative of compound 26 could not be produced in sufficient purity or quantity to study its properties. However, interchanging the terminal $NH_2$ of 26 for an $NO_2$ group, producing compound 31, overcame this constraint and allowed for the production of both the disulfide and its corresponding BITA (Table 3). The disulfide form of compound 31, like 26, was non-toxic and had equivalent NCp7 zinc finger reactivity, even though the $EC_{50}$ increased 2.6-fold (less effective). The BITA form of compound 31 was without antiviral activity. Exploration of ligand extensions with nitro aromatic groups led to compounds 32 to 34 that generally displayed less zinc finger reactivity than the simpler nitro group, as in compound 31. Only the disulfide and BITA forms of compound 34 showed significant antiviral activity.

Repositioning of the sulfonyl group in 3,3'-bis(aminophenyl) sulfones created isomers, compounds 35 and 36, Table 4. These compounds have improved antiviral activities (compound 26 vs. compound 35: $EC_{50}$ 4.3 to 1 mM; 27 vs. 36: $EC_{50}$ 1.5 to 0.62 mM, respectively). However, zinc finger reactivity was significantly reduced (26 vs. 35: 3.3 to 0.92 RFU/min; 27 vs. 36: 5.9 to 2 RFU/min, respectively). In addition, this change decreased the $IC_{50}$ by at least 3-fold (greater toxicity). Thus, the 3,3'-diphenyl sulfone isomers provided no major advantages.

Conversion of the Disulfide to a Novel Thiolester

The action of disulfides on the NCp7 zinc fingers involves a thiol-disulfide interchange between the agent and the CCHC cysteine sulfur atoms. The resulting covalent disulfide linkage between NCp7 and one-half of the drug ("monomeric" portion) causes disruption of the zinc chelate with passive loss of $Zn^{2+}$ ions from the NCp7 structure (see, e.g., Rice (1995) supra; Huang (1998) supra.

To covalently modify zinc finger cysteines through bonds that are more stable than would be possible using any of the compounds described above, novel thioethers were designed and synthesized. To create a thioether link, a moderately active, SH-selective alkylating function at the ortho or meta positions of the benzamide head group was designed. Single-liganded (monomer) benzamides were linked to potentially reactive haloalkanoyl groups via amide or thioester bonds (see Table 5). Compounds 37 through 39 represent amide linkages to either the ortho or meta benzamide positions. Substitution of Cl—$(CH_2)_2$—CO—NH— at either the ortho (compound 37) or meta (compound 38) positions on. the ligand form of compound 2 generated compounds with modest zinc finger reactivity. However, neither had appreciable antiviral activity. Compound 39, having an ortho Cl—$CH_2$—CO—NH—, was completely inactive. Ortho amide substituted probes were synthesized using several other backbones as the ligand structure and gave equivalent results.

Ortho positioned, alkanoyl, aroyl, and haloalkanoyl thioesters were designed and synthesized (compounds 40 to 52, Tables 5 and 6). Synthesis of the acetyl (compound 40), benzoyl (compound 41), 4-methoxybenzoyl (compound 42) and the butyroyl (compound 43) thioesters resulted in four compounds with low µM $EC_{50}$ values and moderate to substantial zinc finger reactivity. However, due to $IC_{50}$ values in the 50 µM range, their antiviral activity approximated that of the BITA derivatives (Table 1).

A new thioester was synthesized using co-haloalkanoyl groups. The ortho 5-bromovaleroyl thioester derivative of compound 2, compound 44, resulted in significantly reduced cytotoxicity and moderate zinc finger activity. The therapeutic index was further enhanced by converting compound 44 to the pyridinioalkanoyl thioester (PATE) derivative, compound 45. The resulting agent demonstrated efficient zinc finger reactivity (3.6 RFU/min), no toxicity at the high test dose of 316 µM and an $EC_{50}$ of less than 10 µM.

Table 6 shows that the PATEs exhibit as a chemotype more favorable antiviral and toxicity profiles than their parental compounds. The lack of toxicity displayed by the pyridiniovaleroyl thioesters is illustrated by their addition to the monobenzamide backbones of compounds 2, 31, 34, 27 and 36, producing the new compounds 45, 47, 50, 51 and 52, respectively, where cellular toxicity of the parent monobenzamide is lessened in all cases. Even though conversion of the compound 23 backbone to the PATE chemotype, resulting in compound 48, did not generate selectivity indexes (TI) of the order found in the other pyridiniovaleroyl thioesters, and failed to reduce monobenzamide toxicity (compound 23 BITA 53.7 µM vs. compound 48 µM), pyridiniovaleroyl thioester conversion partially relieved the toxicity associated with the disulfide form ($IC_{50}$ of compound 23D: 19.4 µM vs. compound 48: 55 µM). Thus, thiolesters, and PATEs in particular, represent a new chemotype which can be used as novel chemotherapeutic agents to target viral zinc fingers.

Antiviral Activity of Pyridinioalkanoyl Thioesters (PATEs)

The 5-bromovaleroyl thioester, compound 44, and two 5-pyridiniovaleroyl thioesters, compounds 45and 47, were analyzed in mechanistic and target-based assays. These compounds did not inhibit HIV-1 integrase, reverse transcriptase or protease enzyme activities (see Table 7). Assays for activity against HIV-1 reverse transcriptase rAdT (template/primer) and rCdG (template/primer) using recombinant HIV-1 reverse transcriptase (S. Hughes, ABL Basic Research NCI-FCRDC, Frederick Md.) were performed as described by Rice (1997) supra. Substrate cleavage of recombinant HIV-1 protease in the presence of test compounds using an HPLC-based methodology with the artificial substrate Ala-Ser-Glu-Asn-Try-Pro-Ile-Val-amide (Multiple Peptide Systems, San Diego Calif.) was performed as described by Rice (1997) supra. The ability of recombinant HIV-1 integrase (S. Hughes, ABL Basic Research NCI-FCRDC, Frederick Md.) to carry out 3' processing and strand transfer activities in the presence of test compounds was performed as described by Buckheit (1994) *AIDS Res. Hum. Retroviruses* 10:1497-1506, and Turpin (1998) *Antimicrob. Agents Chemother.* 42: 487-494.

The 5-bromovaleroyl thioester compound 44 and the two 5-pyridiniovaleroyl thioester compounds 45 and 47 also did not inhibit virus attachment (cell-based p24 attachment assay) and fusion to host cells. The cell-based p24 attachment assay was performed as described in Rice (1995) *Science* 270:1194-1197. Viral inactivation assays were carried out as described in Rice (1995) *Science* 270:1194-1197, and Turpin (1997) supra, with minor modifications. Briefly, MAGI-CCR-5 cells were plated ($4\times10^4$ cells per well) in flat bottomed 2-cm well plates for 24 h, after which the culture media was removed and compound-treated virus was added. The virus used was obtained by transient transfection of pNL4-3 into HeLa cells yielding the replication competent NL4-3 virus. Virus containing supernatants were treated for 2 h at 37° C. after which residual compound was removed by centrifugation (18,000×g, 1 h, 4° C.). Virus pellets were resuspended and placed on the MAGI-CCR-5 monolayers and cultured for 48 h. Monolayers were fixed and stained with X-gal solution and blue cells counted.

Determination of the effect of the test compounds on viral fusion were carried out as follows. Briefly, HL2/3 cells stably expressing HIV-1 Tat and cell surface gp120 and MAGI-CCR-5 cells stably expressing CD4 and CCR5 on their cell surface, containing a β-galactosidase reporter gene under the control of the HIV-1 LTR were pretreated with test compound for 1 h at 37° C. After incubation, the cells were mixed in a 4 to 1 ratio ($2\times10^5$ MAGI-CCR-5 to $8\times10^5$ HL2/3 cells) and co-cultured for 18 h at 37° C.; cultures were fixed and stained with X-gal solution for β-galactosidase activity. Blue cells represented the Tat transactivation of the HV-1 LTR upon fusion of the HL2/3 and MAGI-CCR-5 cells via the CD4/CCR5 co-receptor gp120 interaction.

All three thiolester compounds 44, 45, and 47 promoted metal ion (zinc) ejection from the NCp7 protein, as assessed by the Trp37 assay, described above. These compounds interfered with, and thus could not be tested in, the TSQ fluorochrome assay (see Table 9).

Interaction of zinc finger inhibitors with NCp7 can result in loss of protein structure and their ability to specifically bind oligonucleotides representing the HIV-$1_\psi$packaging site (Huang (1998) supra; Tummino (1997) *Antimicrob. Agents Chemother.* 41:394-400; South (1993) *Protein Sci.* 2:3-19; Dannull (1994) *EMBO J.* 13:1525-1533). The ability of NCp7 to specifically associate with these oligonucleotides after treatment of the protein with a thiolester of the invention was tested. For example, compounds 44, 45 or 47 were very effective at inhibiting Ncp7's ability to associate with target oligonucleotide, as determined using electrophoretic mobility shift assays (EMSA) on nondenaturing polyacrylamide gels. At 1 µM, compound 45 inhibited complex formation. Compounds 44 and 47 inhibited complex formation at 100 µM (see Table 9).

To determine if compound 44, 45 or 47 binding activity was specific for CCHC zinc fingers, a super gel shift EMSA after treatment of K562 cell nuclear extracts with the compounds was performed. This was followed by super shifting with Sp1-specific antibody. Sp1 was chosen because it is a cellular transcription factor that contains three copies of a classical type CCHH zinc finger motif that are required for Sp1 binding to its DNA target. The three compounds 44, 45 or 47 failed to alter the pattern of super shifting of Sp1 bound to its DNA target, indicating that these thiolesters show specificity for the CCHC retroviral Zn finger. Super gel shifting to determine the specificity of zinc finger reactive compounds was carried out using an Sp1 consensus oligomer (Stratagene, La Jolla, Calif.), K562 cell nuclear extracts, and antibodies for Sp1 (Sp1[PEP2]-G) (extracts and Sp1 Abs from Santa Cruz Biotechnology, Inc., Santa Cruz, Calif.). The binding reactions of oligonucleotides with K562 nuclear extract, as well as electrophoretic conditions were carried out as described in the Gelshift Buffer Kit, Stratagene , La Jolla, Calif.

The interaction of zinc finger inhibitors, such as the thiolesters of the invention, with cell-free virus can result in modification of intravirion NCp7 protein and loss of infectivity. Virion-associated NCp7 proteins from cell-free HIV-1$_{MN}$ were treated with thiolester compounds 44 and 45. They were also evaluated by non-reducing Western blotting using HIV-1 NCp7-specific antibodies. The PATE compound 45 resulted in extensive cross-linking of NCp7, whereas its haloalkanoyl thioester precursor (compound 44) was a very poor cross-linking agent. Intravirion NCp7 cross-linking by compound 45 was comparable to DIBA-1, compound 1. Cross-linking by compound 45 was due to formation of intermolecular disulfide bonds because reduction with 2-mercaptoethanol (β-ME) completely reversed the gel retardation. Compound 47 did not effectively initiate NCp7 cross-linking. AZT, a nucleoside reverse transcriptase inhibitor, also failed to cross-link NCp7 (see Table 9).

NCp7 cross-linking is associated with viral inactivation. Whether the ability to crosslink the nucleocapsid protein, as determined by Western blotting, correlated with the ability to inactivate the viruses was tested in a virucidal assay. Virus stocks of HIV-1$_{NL4-3}$ were incubated with various thiolester compounds. The virus was obtained by transient transfection of a replication-competent pNL4-3 plasmid into HeLa cells. Residual thiolester was removed by centrifugation. The virus pellet was resuspended in culture media and used to infect MAGI-CCR-5 cells. At 48 hours post-infection, the cells were washed and stained with X-Gal. Compounds 44 and 45 were virucidal with I$_{50}$ (concentration resulting in 50% virus inactivation) values of 12.3 μM and 13.2 μM, respectively. Although compound 47 was not a potent cross-linker of intravirion NCp7, it was approximately 6-fold (I$_{50}$=2.1 μM) more potent than compounds 44 and 45 at inactivating virus. These data suggest that thiolesters, and compound 47, in particular, form stable adducts with the zinc finger sulfur atoms that do not participate in the generation of intermolecular or intramolecular disulfide cross-linkages.

Analysis of 5-pyridiniovaleric acid (compound 53) without conjugation to a monobenzamide backbone showed significant reactivity in the Trp37 zinc ejection assay (4 RFU/min), even though it was without antiviral activity (see Table 6). Compound 53 was further assessed for intravirion cross-linking of NCp7 and virucidal activity. Neither intravirion cross-linkage of NCp7 nor virucidal activity were detected. Thus, the monobenzamide backbones of compounds 44, 45 and 47 are essential for activity against cell-free virions.

Thiolester compounds were also tested for their ability to inhibit HIV-1 replication in TNFα-induced U1 and ACH-2 cells. U1 cells were induced with 5 ng/ml of TNFα in the presence of various concentrations of the thiolesters 44, 45 or 47. Forty-eight hours later the cultures were characterized for virus p24 antigen production and cell viability. All three compounds inhibited the release of HIV-1 virions (p24) from U1 cells (EC50: 94, 42.2 and 10.7 μM for compounds 44, 45 and 47, respectively) (see Table 9). No cellular toxicity was evident at the high test dose of 100 μM. Higher dose testing (300 μM) of all three thiolesters showed no toxicity for compounds 45 and 47. Compound 44 killed 60% of the cells at 200 μM. Visualization of viral proteins from TNFα-induced U1 cells by electrophoretic separation and immunoblotting (Western blotting) revealed that compounds 45 and 47 induced cross-linking of viral precursor polyproteins and prevented processing of those precursors. Reduction of the U1 protein preparations with β-ME showed that both compound 45 (100 μM) and compound 47 inhibited Pr$^{55gag}$ precursor processing. Compound 44 also induced β-ME reversible alterations in the mobility of zinc finger containing HIV-1 precursor proteins at a intermediate level between compounds 45 and 47. Precursor processing evaluation performed as described by Turpin (1997) *Antiviral Chem. Chemother.* 8:60-69. Thus, thiolester PATEs initiate intracellular disulfide cross-linking of precursor polyproteins during late phase virus assembly and mediate a direct virucidal effect via an attack on the mature NCp7 retroviral zinc fingers in the cell-free virus.

Virion cross linking was performed as described by Rice (1995) *Science* 270:1194-1197 and Turpin (1997) *Antiviral Chem. Chemother.* 8:60-67. Briefly, highly purified HIV-1$_{MN}$ (11.8 μg total protein) was incubated for 2 hour with concentrations of compound. Virions were concentrated and residual compound was removed by centrifugation (18,000×g, 1 h, 4° C.). The viral pellet was solubilized in 0.5 M Tris-HCl, (pH 6.8), 50% glycerol, 8% SDS and 0.4% bromophenol blue and proteins resolved by Western blotting. Western blotting to detect the expression of HIV-1 proteins in U1 cells or virus pellets for virion cross-linking experiments was carried out as described by Turpin (1996) *J. Virol.* 70:6180-6189. Briefly, 50 μg of total cellular protein for U1 experiments or the. total virion pellet (11.8 μg total viral protein) for NCp7 cross linking studies was resolved on 4 to 20% polyacrylamide gels in SDS with Tris-Glycine (Novex, San Diego Calif.). Samples for reduced gels were boiled for 5 min in the presence of 5% β-ME prior to loading. Resolved proteins were electroblotted on to polyvinylidene difluoride (PVDF) membranes, and HIV-1 specific proteins were detected using a mixture of goat anti-HIV-1 NCp7 and p24 or anti-NCp7 for virion proteins alone (a kind gift of L. E. Henderson, AIDS Vaccine Program NCI-FCRDC, Frederick, Md.). Western blots were developed using standard chemiluminescence methodologies, as produced and described by Dupont-NEN, Wilmington, Del.

One significant characteristic of thiolesters is their ability to maintain zinc finger reactivity in the presence of the reducing environment of an in vivo biological fluid. This property can be evaluated, e.g., by testing the compound's resistance to reduction by glutathione under physiologic conditions. This resistance to reduction is a significant improvement over all disulfide containing compounds. For example, the disulfide Nature of DIBAs make them inherently unstable in reducing environments. This results in the disassociation of dimer to monomeric forms and mixed disulfides.

The thiolester PATE compounds 44, 45 and 47 maintained the capacity to attack the cysteine thiols in the presence of a 2 molar excess of glutathione. Thus, conversion of the disulfide to the less nucleophilic 5-bromovaleroyl thioester, as in compound 44, or, 5-pyridiniovaleroyl thioester, as with compounds 45 and 47, confers significant resistance to reductive agents, thus preventing subsequent loss of zinc finger reactivity (see Table 8).

Regarding the Table 10, the activity profile of the PATE chemotype was dependent upon the length of the alkyl spacer between the carbonyl and pyridinio moieties (comparing Compounds 54, 45, and 55). The n=4 spacing appears to be optimal with regard to potency and toxicity. The essential presence of the thiolester sulfur is demonstrated by the inactive Compound 56 where the sulfur is replaced by —NH—. Substituting a chlorine for hydrogen meta to the nitrogen in the pyridinium ring significantly diminishes antiviral potency, possibly due to an electrostatic interaction (repulsive) between the chloro group and residues 39 and 49 of NCp7.

Detecting the Dissociation of a Metal Ion from a Zinc Finger Motif

The invention provides a method and kit to select compounds capable of dissociating a divalent ion chelated with a zinc finger motif. The motif can be isolated, or a substructure of a viral protein or a virion. The method includes contacting the zinc finger with a thiolester; and subsequently detecting the dissociation of the metal ion from the zinc finger protein. The cation is commonly zinc. Any methodology known in the art can be used to detect the dissociation of the metal ion. Exemplary means include, e.g., capillary electrophoresis, immune-blotting, Nuclear Magnetic Resonance (NMR), high pressure liquid chromatography (HPLC), detecting release of radioactive zinc-65, detecting fluorescence, or detecting gel mobility shift, and other techniques which would be apparent to one of skill upon review of this disclosure. These procedures can be practiced with any protocol known in the art, which are well described in the scientific and patent literature. A few exemplary techniques are set forth below.

As the invention also provides a genus of novel thiolesters capable of dissociating a metal ion from a zinc finger in vitro, detection of the dissociation of the metal ion identifies a thiolester specie within the scope of the invention. The zinc ejection assay was used as a first line screen to identify thiolesters within the scope of the invention. One strategy for such screening used the XTT cytoprotection assay to monitor antiviral activity and the Trp37 zinc ejection assay to identify thiolesters able to act at the cellular level on the NCp7 protein or its Gag or Gag-Pol precursors.

A thiolester is within the scope of the invention if it is capable of any level of cation ejection from a zinc finger. In fact, a thiolester capable of zinc ejection at a low rate, i.e., with slow kinetics, is preferable for some uses, especially for certain in vivo applications. An exemplary "weak cation ejector" thiolester of the invention is compound 50, with a zinc ejection rate of 0.86 RFU/min as measured by the Trp37 zinc finger fluorescence assay. However, thiolesters with lower ejection rates (<0.86 RFU/min) are also within the scope of the invention. A "high" ejection rate would be in the range of approximately 8 RFU/min. Thiolesters with an antiviral activity $EC_{50}$ of <15 uM were selected as preferred embodiments.

Capillary Zone Electrophoresis (CZE)

Retroviral zinc finger proteins complex with two zinc ions, each with a formal charge of $^+2$. Reagents that react with the protein and remove the zinc ions cause a change in the conformation and charge of the protein. Thus, the electrophoretic mobility of the reacted protein will differ from the mobility of the unreacted protein. Changes in electrophoretic mobility of the protein can easily be detected by the standard technique of capillary zone electrophoresis (CZE). For a general description of CZE, see, e.g., *Capillary Electrophoresis, Theory and Practice* (Academic Press, Inc. Grossman and Colburn (eds.) (1992).

Generally, electrophoretic mobility of the protein (at a pH determined by the buffer in the capillary electrophoresis tube) is used to move the retroviral protein from a fixed starting position towards one electrode. The migration rate may be monitored by UV absorption, e.g., at 215 nm. Sample tubes containing an appropriate amount of a solution comprising the retroviral NC protein of choice, with and without the thiolester compound to be tested for CCHC zinc finger inactivation, are placed in an automatic sample injector. At programmed intervals, samples are drawn into the capillary tube and the UV absorption is monitored. Unmodified retroviral NC protein gives a sharp peak of migrating protein passing the detector. Modifications of the protein, caused by reaction with the test compound of choice, are revealed by a change in the electrophoretic mobility of the reacted protein.

Capillary zone electrophoresis has the advantage of simple automation, since many different samples can be loaded and analyzed in successive runs. Each run requires about 10 minutes and each sample tube can be analyzed multiple times. An example of a kit utilizing CZE for analysis of selected compounds to be tested for CCHC zinc finger reactivity would contain about 100 micrograms (μg) of purified retroviral NC protein complexed with zinc in, for example, 1.0 ml of water, and could be used for the testing of approximately 1000 test compounds.

Release of Radioactive Zinc from Zinc-65 Labeled NCp7

Purified HIV-1 NCp7 can be reconstituted with radioactive zinc-65 with a determined specific activity. By monitoring the release of radioactive zinc-65 caused by the reaction of a test compound with a retroviral NC protein, it is possible to determine the reactivity of the test compound.

A thiolester test compound can be added to a solution containing the NC protein complexed with radioactive zinc-65. Following the reaction, protein (reacted and unreacted) can be precipitated, for example, by immunoprecipitation or immunoadsorbtion methods using known antibodies, or by the addition of a calibrated amount of nucleic acid such that the NC protein saturates the binding sites on the nucleic acid matrix. Under conditions of low ionic strength, the saturated protein-nucleic acid complex forms a precipitate that can be removed by centrifugation. Alternatively, labeled nucleocapsid protein may be attached to a solid support, and test reagents added directly to the attached protein. Any reactions releasing zinc from the protein can be detected by the release of radioactive zinc-65 into the soluble supernatant. This general procedure can be automated depending on the equipment available.

A kit supplying retroviral nucleocapsid protein and appropriate precipitating agents can be used to detect the ability of test compounds to remove zinc from the protein.

Release of Radioactive Zinc from Zinc-65 Labeled Whole Virus

Zinc is present in virus in quantities nearly stoichiometric with CCHC zinc finger arrays (Bess (1992) *J. Virol.* 66:840). Nearly all of the zinc is coordinated in the CCHC arrays (Summers (1992) *Protein Science.* 1:563). Therefore, zinc released from a virus derives from zinc previously coordinated in CCHC arrays, rather than from unrelated proteins or other non-specific associations with the virion.

Purified virus can be produced from cells cultured in the presence of added zinc-65. Labeled virus can be isolated and purified by density gradient centrifugation in the presence of added EDTA to remove any unbound zinc. The purified virus can be any retrovirus of interest including, but not limited to, HIV-1, HIV-2 or SIV.

Compounds to be tested (thiolesters of the invention) can be added to the purified radioactive virus under conditions appropriate for the test compound of choice (Rice (1993) *Nature* 361:473-475). Following the reaction, removal and/or inactivation of the reagent, the virus is disrupted by the addition of a non-ionic detergent (e.g., Triton X-100), and the viral core containing the NC protein complexed to nucleic acid is removed by centrifugation.

Radioactive zinc-65 released into the supernatant indicates that the test compound penetrated the intact virus and disrupted the NC protein-zinc complex. Kits to determine whether test compounds can remove retroviral NC-chelated zinc would contain, for example, intact retrovirus particles with radioactive zinc-65 incorporated into their NC proteins, appropriate reaction buffers and a non-ionic detergent.

Fluorescence-Based Detection of Zinc Dissociation from Protein

Changes in the intrinsic fluorescence of aromatic protein moieties are commonly used to monitor a reaction which involves a change in protein conformation. In the present invention, fluorescence can be used to monitor the loss of metal ion from a zinc finger, e.g., the loss of zinc from a CCHC retroviral zinc finger protein, after contact with a thiolester of the invention. The intrinsic fluorescence of Trp37 in the second zinc finger of HIV-1 NC protein has been used to monitor nucleic acid binding and conformation of the zinc finger complex (see, Summers (1992) supra).

Zinc ejection is measured by the ability of compounds to chemically attack the cysteines in purified NCp7 protein resulting in a loss of fluorescence due to the. movement of the tryptophan 37 residue from an exposed to an internal position on the protein. Zinc ejection is measured and expressed as either percent decrease in total fluorescence or decrease in relative fluorescence units per min during a 30 min assay (RFU/min). A thiolester is considered within the scope of the invention if any amount of zinc ejection is detected. For example, compound 50 has a zinc ejection rate of 0.86 RFU/min.

Artificial fluorescent probes can also be incorporated into a protein to provide for the detection of changes in conformation. Poly ethino-adenine, e.g., can be used as a fluorescent nucleotide to measure the extent of thiolester-zinc finger interaction (see, Karpel (1987) *J. Biol. Chem* 262:4961).

Finally, a variety of known fluorescent zinc chelators capable of complexing liberated zinc may be used to monitor zinc loss. By monitoring the release of zinc from the CCHC zinc finger arrays, the effect of a given reagent may be determined (Rice (1996) *J. Med. Chem.* 39:3606-3616; Rice (1996) *Science* 270:1194-1197).

Detection of Disulfide Cross-Linked NC Protein by Gel-Mobility Shift Assays

Purified concentrated retrovirus and antisera against the purified NC protein of the virus can be used to test the ability of a specific compound to penetrate the virus and react with the NC protein by forming disulfide complexes in the core of the virus. Compound are mixed with the whole retrovirus under reaction conditions appropriate for the compound. The virus is then removed from the reagent by centrifugation and disrupted in, e.g., standard SDS-PAGE sample buffer with (reduced) and without (non-reduced) 2-mercaptoethanol. The viral proteins are then separated by standard SDS-PAGE and the sample examined for the presence or absence of the monomeric zinc finger protein in the non-reduced sample. Depending upon the virus used in the experiment and the conditions of electrophoresis, the zinc finger protein can be visualized by protein staining methods, or by immuno-blot methods. Compounds which react with the zinc finger protein by attacking the zinc finger complexes and forming disulfide cross-linked products inactivate the virus. Thus, compounds of interest (i.e., those which cause cross-linking), including the thiolesters of the invention, reduce the amount of monomeric zinc finger protein detected. For example, thiolester compound 45 is a strong cross-linker of intravirion NCp7 resulting in complete loss of monomeric NCp7 as detected by Western blotting.

The thiolester-treated virions can also be tested for infectivity. The virions are suspended in media (rather than solubilized) and added to target cells. The cultures are then examined to determine whether the virions are still active. To determine whether the treated virus particles are active, the cells are monitored for the presence of intracellularly-synthesized viral RNA using, for example, the polymerase chain reaction (PCR) (Rice (1993) *Proc. Natl. Acad. Sci. USA* 90:9721;Turpin (1996) *J. Virol.* 70:6180). Alternatively, cytoprotection assays can be used (Weislow (1993) *J. Natl. Cancer Inst.* 81:577).

An example of a compound which can be used as a control in the gel mobility shift assay is azodicarbonamide (ADA), a compound which is commercially available from the Aldrich Chemical Company (Milwaukee, Wis.). ADA also inactivates HIV-1 virus, as determined using the PCR assay described above.

A kit incorporating the gel-mobility shift concept can be used to identify and study thiolesters which are able to penetrate intact virus and to induce disulfide cross-links in the viral zinc finger proteins. Such a kit would contain, for example, purified concentrated retrovirus and appropriate size standards to monitor the change in mobility through the gel due to disulfide cross-linking.

High Pressure Liquid Chromatography (HPLC) Purified NC Proteins for Structural Characterization of Reaction Products Highly purified retroviral zinc finger proteins can be produced by expression from vectors generated through recombinant DNA technology. These proteins when reconstituted with zinc, as described by Summers (1992) *Protein Science* 1:563-567, provide the source of the NC proteins containing the zinc fingers that are the targets for attack by the thiolester compounds of this invention. When the zinc fingers proteins react with identified compounds, the reaction produces a covalent change in the zinc finger protein, and the modified protein can be separated from the unreacted protein by, for example, reversed phase HPLC.

The purified proteins and these separation methods are used to obtain sufficient modified protein (i.e., products of the reaction) for chemical and structural analysis. The purified reaction products are isolated and their structures determined by standard N-terminal Edman degradation. However, for any specific reagent, the gradients and HPLC conditions will depend upon the NC protein and the reaction products.

This procedure is used to identify thiolester compounds which react with HIV-1 zinc fingers. The reaction conditions and HPLC conditions for the data presented were similar to those described above.

Kits standardizing these techniques may be constructed such that they contain, for example, purified retroviral zinc finger proteins.

Nuclear Magnetic Resonance-Based Detection of Zinc Loss

NMR can be used to monitor the loss of zinc from retroviral zinc finger proteins (see, e.g., Rice (1993) *Nature* 361:473475; McDonnell (1997) *J. Med. Chem.* 40:1969; Rice (1997) *Nature Medicine* 3:341-345). It is expected that one of skill is familiar with the general technique of NMR and its many applications to monitor protein-ligand interactions. Briefly, the atoms in retroviral zinc finger proteins bound to zinc share a different local environment than zinc finger proteins which lack zinc. The difference in local environment leads to distinct NMR spectra for protein molecules which bind zinc, versus those that do not. By monitoring, for example, the proton ($^1$H) spectrum of a sample containing metal ion-chelated zinc finger protein and a compound of the present invention over time, it is possible to measure whether the compound causes the protein to loose its zinc ion.

Since NMR can be used to provide the percent of protein molecules which are bound to zinc over time, it is also possible to use this technique to define the reaction kinetics of a given reaction. Similarly, NMR may be used to monitor the effect of test compounds upon the binding of zinc finger proteins to nucleic acid complexes. Kits containing e.g., purified retroviral zinc finger proteins and oligonucleotides may be used to standardize the practice of this method.

Determining Thiolester Anti-Viral Activity

A thiolester is within the scope of the invention if it displays any antiviral activity (i.e., any ability to decrease or diminish the transmission of or the replicative capacity of a virus). The antiviral activity can be determined empirically by clinical observation or objectively using any in vivo or in vitro test or assay, e.g., the XTT cytoprotection assay (described herein), measuring Tat-induced activity (as in the HeLa-CD4-LTR-beta-gal (MAGI cells) assay and detecting Tat-induced beta-galactosidase activity, see, e.g., Tokunaga (1998) *J. Virol.* 72:6257-6259), and the like. A thiolester with any degree of measurable antiviral activity is within the scope of the invention even if no metal ion dissociation is detectable.

One exemplary means to determine antiviral activity is with CEM-SS cells and virus (e.g., HIV-1RF) (MOI=0.01) using the XTT (2,3-bis[2-methoxy-4-nitro-5-sulfophenyl]-5-[(phenylamino)carbonyl]-2H-tetrazolium hydroxide) cytoprotection assay, as described by Rice (1993) *PNAS* 90:9721-9724, and Rice (1997) *Antimicrob. Agents Chemother.* 41:419-426. Briefly, cells are infected with HIV-1 RF (or other virus to be tested) in the presence of various dilutions of test compounds (thiolesters and controls). The cultures are incubated for seven days. During this time control cultures without protective compounds (i.e., compounds with anti-viral activity) replicate virus, induce syncytia, and result in about 90% cell death. The cell death is measured by XTT dye reduction. XTT is a soluble tetrazolium dye that measures mitochondrial energy output, similar to MTT. Positive controls using dextran sulfate (an attachment inhibitor) or 3'-Azido-2'-3'-dideoxythymidine, AZT (a reverse transcriptase inhibitor) are added to each assay. Individual assays are done in duplicate using a sister plate method.

Effective antiviral concentrations providing 50% cytoprotection ($EC_{50}$), and cellular growth inhibitory concentrations causing 50% cytotoxicity ($IC_{50}$) are calculated.

Alternatively, any virus can be grown in culture, or in an in vivo (animal) model, in the presence or absence of a thiolester or a thiolester-containing pharmaceutical formulation to test for anti-viral, viral transmission-inhibiting activity and efficacy. Any virus, assay or animal model which would be apparent to one of skill upon review of this disclosure can be used, see, e.g., Lu (1997) *Crit. Rev. Oncog.* 8:273-291; Neildez (1998) *Virology* 243:12-20; Geretti (1998) *J. Gen. Virol.* 79:415-421; Mohri (1998) *Science* 279:1223-1227; Lee (1998) *Proc. Natl. Acad. Sci. USA* 95:939-944; Schwiebert (1998) *AIDS Res. Hum. Retroviruses* 14:269-274.

For in vitro assays, any measurable decrease in the viral load of a culture grown in the presence of a thiolester test compound as compared to a positive or negative control compound is indicative of an anti-viral, transmission-inhibiting effect. Typically, at least a 30% reduction in viral load observed, generally, between 10% and 99%. As discussed in definition section, above, any relevant criteria can be used to evaluate the antiviral efficacy of a thiolester composition or thiolester-containing formulation.

Cloning and Expression of Retroviral Nucleocapsid Proteins

The novel thiolesters of the invention are capable of dissociating a metal ion from a zinc finger in vitro. Zinc finger containing proteins are used to detect the dissociation of a metal ion from a zinc finger motif and in the methods and kits of the invention. General laboratory procedures for the cloning and expression of zinc finger motifs and proteins containing these motifs can be found, e.g., current editions of Sambrook, et al., Molecular Cloning *A Laboratory Manual* (2nd Ed.), Vol. 1-3, Cold Spring Harbor Laboratory, Cold Spring Harbor, N.Y., 1989; CURRENT PROTOCOLS IN MOLECULAR BIOLOGY, Ausubel, ed. Greene Publishing and Wiley-Interscience, New York (1987). Sequences and sources of zinc fingers, including nucleic acids, proteins and viral sources, are publicly available, for example, through electronic databases, such as, e.g., The National Center for Biotechnology Information at http://www.ncbi.nlm.nih.gov/Entrez/, or, The National Library of Medicine at http://www.ncbi.nlm.nih.gov/PubMed/.

The nucleic acid compositions that may be used to express zinc finger-containing proteins, whether RNA, cDNA, genomic DNA, or a hybrid of the various combinations, can be isolated from natural sources, or may be synthesized in vitro. Recombinant DNA techniques can be used to produce polypeptides. In general, the DNA encoding the polypeptide or peptide of interest are first cloned or isolated in a form suitable for ligation into an expression vector. After ligation, the vectors containing the DNA fragments or inserts are introduced into a suitable host cell for expression of the recombinant polypeptides. The polypeptides are then isolated from the host cells. The nucleic acids may be present in transformed or transfected whole cells, in a transformed or transfected cell lysate, or in a partially purified or substantially pure form. Techniques for nucleic acid manipulation of genes encoding zinc finger-containing proteins, such as subcloning nucleic acid sequences into expression vectors, labeling probes, DNA hybridization, and the like are described, e.g., in Sambrook and Ausubel, supra.

Once the DNAs are isolated and cloned, one can express the desired polypeptides in a recombinantly engineered cell such as bacteria, yeast, insect, or manmalian cells. It is expected that those of skill in the art are knowledgeable in the numerous expression systems available for expression of the recombinantly produced proteins. No attempt to describe in detail the various methods known for the expression of proteins in prokaryotes or eukaryotes will be made. In brief summary, the expression of natural or synthetic nucleic acids encoding polypeptides will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding recombinant polypeptides. To obtain high level expression of a cloned gene, it is desirable to construct expression plasmids which contain, at the minimum, a promoter to direct transcription, a ribosome binding site for translational initiation, and a transcription/translation terminator.

Thiolesters as Viricidals

The invention provides a composition comprising a bio-organic or other material and an amount of a thiolester of the invention effective to inactivate any virus (susceptible to inactivation by a thiolester) which is or may contaminate the material. The material can be bio-organic, such as, e.g., blood plasma, nutrient media, protein, a pharmaceutical, a cosmetic, a sperm or oocyte preparation, cells, cell cultures, bacteria, viruses, foods, drinks. They can be surgical or other medical materials, such as, e.g., implant materials or implantable devices (e.g. plastics, artificial heart valves or joints, collagens), medical materials (e.g., tubing for catheterization, intubation, IVs) and containers (e.g., blood bags, storage containers), and the like. Alternatively, a thiolester of the invention can be in the form of a composition which is applied to any of the above materials as a viricidal reagent and removed before the material's use. The viricidal composition can contain a mixture of different thiolesters of the invention in varying amounts. For example, thiolesters can be added to cell cultures to reduce the likelihood of viral contamination, providing added safety for the laboratory workers.

Thiolesters as Pharmaceutical Formulations

The invention also provides pharmaceutical formulations comprising the thiolesters of the invention. These thiolesters are used in pharmaceutical compositions that are useful for administration to mammals, particularly humans to for the treatment of viral, especially retroviral, infections.

The thiolesters of the invention can be formulated as pharmaceuticals for administration in a variety of ways. Typical routes of administration include both enteral and parenteral. These include, e.g., without limitation, subcutaneous, intramuscular, intravenous, intraperitoneal, intramedullary, intrapericardiac, intrabursal, oral, sublingual, ocular, nasal, topical, transdermal, transmucosal, or rectal. The mode of administration can be, e.g., via swallowing, inhalation, injection or topical application to a surface (e.g., eyes, mucous membrane, skin). Particular formulations typically are appropriate for specific modes of administration. Various contemplated formulations include, e.g., aqueous solution, solid, aerosol, liposomal and transdermal formulations. Details on techniques for formulation and administration are well described in the scientific and patent literature, see, e.g., the latest edition of "Remington's Pharmaceutical Sciences" (Mack Publishing Co, Easton Pa.).

Aqueous Solutions for Enteral, Parenteral or Transmucosal Administration

Examples of aqueous solutions that can be used in formulations for enteral, parenteral or transmucosal drug delivery include, e.g., water, saline, phosphate buffered saline, Hank's solution, Ringer's solution, dextrose/saline, glucose solutions and the like. The formulations can contain pharmaceutically acceptable auxiliary substances to enhance stability, deliverability or solubility, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

Aqueous solutions are appropriate for injection and, in particular, for intravenous injection. The intravenous solution can include detergents and emulsifiers such as lipids. Aqueous solutions also are useful for enteral administration as tonics and administration to mucous or other membranes as, e.g., nose or eye drops. The composition can contain a thiolester in an amount of about 1 mg/ml to 100 mg/ml, more preferably about 10 mg/ml to about 50 mg/ml.

Formulations for Enteral or Transdermal Delivery

Solid formulations can be used for enteral administration. They can be formulated as, e.g., pills, tablets, powders or capsules. For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10%-95% of active ingredient.

A non-solid formulation can also be used for enteral (oral) administration. The carrier can be selected from various oils including those of petroleum, animal, vegetable or synthetic origin, e.g., peanut oil, soybean oil, mineral oil, sesame oil, and the like. See Sanchez, et al., U.S. Pat. No. 5,494,936. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Nonionic block copolymers synthesized from ethylene oxide and propylene oxide can also be pharmaceutical excipients; copolymers of this type can act as emulsifying, wetting, thickening, stabilizing, and dispersing agents, see, e.g., Newman (1998) *Crit. Rev. Ther. Drug Carrier Syst.* 15:89-142.

A unit dosage form, such as a tablet, can be between about 50 mg/unit to about 2 grams/unit, preferably between about 100 mg/unit to about 1 gram/unit.

Topical Administration: Transdermal/Transmucosal Delivery

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays, for example, or using suppositories.

For topical administration, the agents are formulated into ointments, creams, salves, powders and gels. In one embodiment, the transdermal delivery agent can be DMSO. Transdermal delivery systems can also include, e.g., patches.

The thiolesters can also be administered in sustained delivery or sustained release mechanisms, which can deliver the formulation internally. For example, biodegradeable microspheres or capsules or other biodegradeable polymer configurations capable of sustained delivery of a composition can be included in the formulations of the invention (see, e.g., Putney (1998) *Nat. Biotechnol.* 16:153-157).

Formulation Delivery by Inhalation

For inhalation, the thiolester formulation can be delivered using any system known in the art, including dry powder aerosols, liquids delivery systems, air jet nebulizers, propellant systems, and the like. See, e.g., Patton (1998) *Biotechniques* 16:141-143; inhalation delivery systems by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like.

For example, the pharmaceutical formulation can be administered in the form of an aerosol or mist. For aerosol administration, the formulation can be supplied in finely divided form along with a surfactant and propellant. The surfactant preferably is soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides can be employed. The surfactant can constitute 0.1%-20% by weight of the composition, preferably 0.25%-5%. The balance of the formulation is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve. See, e.g., Edwards (1997) *Science* 276:1868-1871.

A nebulizer or aerosolizer device for administering thiolesters of this invention typically delivers an inhaled dose of about 1 mg/m$^3$ to about 50 mg/m$^3$.

Delivery by inhalation is particular effective for delivery to respiratory tissues for the treatment of respiratory conditions including an inflammatory component.

Other Formulations

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. For a general discussion of pharmacokinetics, See, *Remington's Pharmaceutical Sciences*, supra, Chapters 37-39.

Administration

The thiolester of the invention are used in the treatment and prevention of viral infection, particularly, retroviral infections. The amount of thiolester adequate to accomplish this is defined as a "therapeutically effective dose." The dosage schedule and amounts effective for this use, i.e., the "dosing regimen," will depend upon a variety of factors, including frequency of dosing, the stage of the disease or condition, the severity of the disease or condition, the general state of the patient's health, the patient's physical status, age and the like. In calculating the dosage regimen for a patient, the mode of administration also is taken into consideration.

The dosage regimen must also take into consideration the pharmacokinetics, i.e., the thiolester's rate of absorption, bioavailability, metabolism, clearance, and the like (see, e.g.; the latest Remington's edition, supra).

Single or multiple administrations of the compositions can be carried out with dose levels and pattern being selected by the treating physician. In any event, the pharmaceutical formulations should provide a quantity of a thiolester sufficient to treat the patient effectively. The total effective amount of a thiolester of the present invention can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a thiolester of the present invention required to obtain an effective dose in a subject depends on many factors including, e.g., the pharmacokinetics of the prodrug and of its hydrolysis product, the age and general health of the subject, the route of administration, the number of treatments to be administered and the judgment of the prescribing physician. In view of these factors, the skilled artisan would adjust the dose so as to provide an effective dose for a particular use.

Vaccine Formulations Comprising the Thiolesters of the Invention

The invention also provides an isolated and inactivated virus, where the virus is inactivated by a method comprising contacting the virus with a thiolester compound of the invention, wherein contacting said virus with said compound inactivates said virus. In one embodiment the isolated and inactivated virus further comprises a vaccine formulation. A vaccine formulation of the invention can also comprises an isolated thiolester-complexed viral protein.

The thiolester-complexed, inactivated viruses of the invention are used in vaccine formulations that are useful for administration to mammals, particularly humans to treat and generate immunity to of a variety of viral diseases, particularly retroviral infections, such as HIV-1. The vaccine formulations can be given single administrations or a series of administrations. When given as a series, inoculations subsequent to the initial administration are given to boost the immune response and are typically referred to as booster inoculations.

The vaccines of the invention contain as an active ingredient an immunogenically effective amount of a thiolester-complexed, inactivated, virus. Useful carriers are well known in the art, and include, e.g., thyroglobulin, albumins such as human serum albumin, tetanus toxoid, polyamino acids such as poly(D-lysine: D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are also advantageously used to boost an immune response.

Uses of Thiolester Inactivated Viruses and Thiolester-Complexed Proteins

In addition to uses as vaccines, thiolester-inactivated viruses and thiolester-complexed viral proteins have a variety of uses. For example, thiolester-complexed viral proteins or thiolester-inactivated viruses can be used as reagents for the detection of corresponding anti-viral antibodies. A very commonly used test to determine if an individual is infected with a virus, such as HIV, is to screen for the presence of antiviral antibodies. Thiolester-inactivated virion or thiolester-complexed viral protein can be used in these detection tests as trapping antigens or control antigens. See, e.g., Hashida (1997) *J. Clin. Lab. Anal.* 11:267-286; Flo (1995) *Eur. J. Clin. Microbiol. Infect. Dis.* 14:504-511.

Thiolester-inactivated virion or thiolester-complexed viral protein can be used as crystallization reagents for X-ray crystallization analysis or other ultrastructural studies, see, e.g., Yamashita (1998) *J. Mol. Biol.* 278:609-615; Wu (1998) *Biochemistry* 37:4518-4526. They can also be used as molecular weight, pI or other controls in various physiochemical experiments and methodologies.

Kits and Apparatus

In an additional aspect, the present invention provides kits embodying the methods and apparatus herein. Kits of the invention optionally comprise one or more of the following: (1) a thiolester or thiolester component as described herein; (2) instructions for practicing the methods described herein, and/or for using the thiolester or thiolester component; (3) one or more assay component; (4) a container for holding thiolesters, assay components, or apparatus components useful for manipulating thiolesters or practicing the methods herein, and, (5) packaging materials.

In a further aspect, the present invention provides for the use of any compound, apparatus, apparatus component or kit herein, for the practice of any method or assay herein, and/or for the use of any apparatus or kit to practice any assay or method herein.

Uses of Thiolesters

In a further aspect, the present invention provides for the use of any thiolester composition, virus, inactivated virus or viral component, cell, cell culture, mammal, apparatus, apparatus component or kit herein, for the practice of any method or assay herein, and/or for the use of any apparatus or kit to practice any assay or method herein and/or for the use of viruses, cells, cell cultures, compositions or other features herein as a medicament. The manufacture of all components herein as medicaments for the treatments described herein is also provided and apparent upon review of the foregoing.

The invention will be described in greater detail by way of specific examples. The following examples are offered for illustrative purposes, and are intended neither to limit or define the invention in any manner.

EXAMPLES

Example 1

Capillar Electrophoresis

One exemplary means to determine the metal ion displacing capability of a thiolester of the invention is through capillary electrophoresis. The NCp7 protein complexes two zinc ions, each with a formal charge of +2. Reagents that react with the protein and remove the zinc ions cause a change in the conformation and charge of the protein. Thus the electrophoretic mobility of the reacted protein will differ from the mobility of the unreacted protein. Changes in electrophoretic mobility of the protein can easily be detected by capillary zone electrophoresis (CZE).

The capillary column buffer is 0.001 M sodium phosphate at pH 3.0, and protein are detected by UV absorption at 215 nm. The sample tubes can contain about 10 or more microliters of a solution consisting of 0.25 micrograms of NCp7 per ml in water at pH 7.0, with or without added zinc finger reactive composition, e.g., a thiolester of the invention. Sample tubes are placed in an automatic sample injector. At programmed intervals 10 µL of sample are drawn into the capillary column and the data was collected as UV absorption per minute. Unmodified p7NC gives a sharp peak of migrating protein passing the detector in about 7.95 minutes. Modifications of the protein, caused by reaction with the test compound of choice, are revealed by a change in this pattern.

Capillary electrophoresis has the advantage of simple automation, since many different samples can be loaded into the sample holding rack and analyzed in successive runs. Each run requires about 10 minutes and each sample tube can be analyzed many times.

Example 2

Preparation of N-[2-(5-Pyridiniovaleroylthio)benzoyl]-3-amino progionamide Bromide (YS1332D)—Templates VI and VII, and N-[2-(5-Pyridiniovaleroylthio)glycinamide Bromide (YS1333D—Templates V and VII)

Synthesis of YS1332A, a Disulfide Benzamide Intermediate 2,2'-Dithiodibenzoyl chloride (3.43 g, 10 mmol) was added to a clear solution of β-alanine amide hydrochloride (NOVA Biochem) (3.1 g, 25 mmol) and 4-methylmorpholine (NMM; 5 ml, 45 mmol) in N,N-dimethylacetamide (DMA; 30 ml) and water (5 ml) at room temperature (RT). The mixture changed to clear reddish-brown solution in 30 min. The solution was stirred at RT for 3 days, during which a precipitate was formed. The mixture was added to 1M HCl (500 ml). The resulting yellow-orange precipitate was collected, washed with water and dried under vacuum. Yield was 2.93 g (65%).

YS1333A was synthesized similar to YS1332A, but the reaction time was 1 day, not 3 days. Yield was 4 g (95%).

Synthesis of YS1332B, Reduction of YS1332A to a Thiol Intermediate

To the mixture of YS1332A (2 g, 4.5 mmol) in DMF (18 ml) and water (2 ml) was added tris(2-carboxyethyl)phosphine hydrochloride (1.5 g, 5.2 mmol) and triethylamine (0.5 ml) at RT. The mixture changed to a clear orange solution in 5 min. It was stirred for 1 h, and then added to ethyl ether (200 ml). The precipitate was collected, washed with water (3×20 ml) and dried under vacuum. Yield was 1.56 g (77%) of white product.

YS1333B was made in the same manner as YS1332B. Yield was 1.5 g (76%).

Synthesis of YS1332C, a Haloalkanoyl Thioester Intermediate

To a solution of YS1332B (0.8 g, 3.6 mmol) in DMA (5 ml) was added 5-bromovaleryl chloride (1.4 ml, 10.8 mmol) at RT under nitrogen. The mixture was stirred for 1 h, then added to ethyl ether (80 ml). The precipitate was collected and dissolved in DMF (5 ml). The solution was added to 10% sodium bicarbonate (40 ml; pH=8) with stirring. The white precipitate was collected, washed with water and dried. Yield was 0.83 g (70%).

YS1333C was made the same way as YS1332C. Yield was 1.27 g (74%).

Synthesis of YS1332D, a Pyridinioalkanoyl Thioester (PATE)

A solution of YS1332C (0.2 g, 0.52 mmol) in pyridine (4 ml) was stirred at RT under nitrogen overnight. The mixture was added to ethyl ether (40 ml). The white precipitate was collected, washed with ether and dried. Yield was 0.23 g (95%).

YS1333D was made in a similar manner to YS1332D, but the reaction mixture was stirred for 2 days, not 1 day. Yield was 0.22 g (90%).

Example 3

Preparation of N-[2-(5-Pyridiniovaleroylthio)benzoyl]-3-aminopropionic Acid Bromide (YS1334D)—Templates VI and VII, and N-[2-(5-Pyridiniovaleroylthio)benzoyl]-L-isoleucine Bromide (YS1324D)—Templates V and VII Synthesis of YS1334A, a Disulfide Benzamide Intermediate 2,2'-Dithiodibenzoyl chloride (3.43 g, 10 mmol) was added to a clear solution of β-alanine t-butyl ester hydrochloride (NOVA Biochem) (4.8 g, 25 mmol) and 4-methylmorpholine (NMM; 5 ml, 45 mmol) in N,N-dimethylacetamide (DMA; 10 ml) at room temperature (RT). The mixture was stirred at RT overnight. To it was added heptane (200 ml). The resulting precipitate was dissolved in a small amount of DMF, then added to 1M HCl (500 ml). The viscous solid precipitate was collected, washed with water and dried under vacuum. Yield was 5.1 g (91%)

YS1322A was synthesized in the same way from 5.0 mmol of starting dichloride and an excess of L-isoleucine t-butyl ester hydrochloride. Yield was 3.10 g (65%) of the disulfide.

Synthesis of YS1334B, Reduction of YS1334A to a Thiol Intermediate

To a solution of YS1334A (1.8 g, 3.2 mmol) in DMF (9 ml) and water (1 ml) was added tris(2-carboxyethyl)phosphine hydrochloride (1.3 g, 4.5 mmol) and triethylamine (0.45 ml) at RT. The mixture was stirred for 1 h, and then added to 0.5 M HCl (200 ml). The viscous residue was collected, washed with water and dried under vacuum. Yield was 1.24 g (69%).

YS1324A was made in the same way as YS1334B. 2.0 g of disulfide yielded 1.5 g of thiol (75%).

Synthesis of YS1334C, a Haloalkanoyl Thioester Intermediate

To a solution of YS1334B (1.24 g, 4.4 mmol) in DMA (5 ml) was added 5-bromovaleryl chloride (1.5 ml, 11 mmol) at RT under nitrogen. The mixture was stirred for 1 h, then added to ethyl ether (100 ml). The solvent was evaporated to 5 ml, and the resulting viscous residue was separated, washed with 10% sodium bicarbonate (20 ml; pH=8) and water (40 ml), and dried. Yield was 1.6 g (82%).

YS1324B was prepared from 1.0 g of the thiol to yield 0.95 g of product (65% yield).

Synthesis of YS1334D, a Pyridinioalkanoyl Thioester (PATE)

A solution of YS1334C (1.6 g, 3.6 mmol) in pyridine (10 ml) was stirred at RT under nitrogen overnight. It was then added to a solution of ethyl ether (200 ml) and heptane (100 ml). The precipitated phase was dissolved in methanol (5 ml) and added to a solution of ether (80 ml) and heptane (200 ml). The precipitate was dissolved in a solution of trifluoroacetic acid (10 ml) and formic acid (3 g). The solution was stirred at RT overnight and was reduced to 5 ml with a stream of nitrogen. To the residue was added ethyl ether (40 ml). The precipitate was collected and dried. Yield was 0.9 g (53%).

YS1324D was prepared from 0.60 g of the corresponding bromovaleroyl thioester to yield 0.58 g (58%) of the isoleucine-bearing PATE.

The foregoing is offered for purposes of illustration. It will be readily apparent to those skilled in the art that the materials, procedural steps and other parameters of the methods and kits described herein may be further modified or substituted in ways without departing from the spirit and scope of the invention.

What is claimed is:

1. A method for inactivating a retrovirus comprising a protein comprising a zinc finger, said method comprising contacting said retrovirus with a compound having the formula:

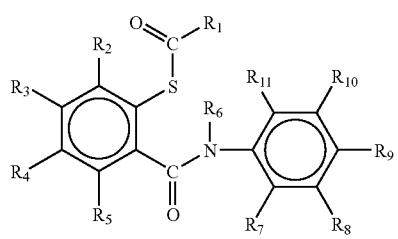

Template I wherein:

$R_1$ is Y—Z;

Y is —$(CH_2)_m$—, wherein m is an integer from 1 to 6;

Z is pyridinio having the structure:

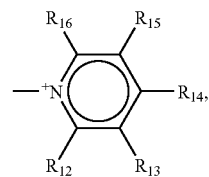

wherein $R_2$, $R_3$, $R_4$, $R_5$, $R_6$, $R_7$, $R_8$, $R_{10}$, $R_{11}$, $R_{12}$, $R_{13}$, $R_{14}$, $R_{15}$, and $R_{16}$, are -H; and $R_9$ is (O=S=O)-G', wherein G' is selected from the group consisting of —$NH_2$, —NH-alkyl, —NH-acyl groups, nitroaryl, and aryl-NH-acyl;

wherein contacting said retrovirus with said compound inactivates said retrovirus.

2. The method of claim 1, wherein said compound administered to inhibit the transmission of the retrovirus.

3. The method of claim 1, wherein said compound is administered intra-vaginally or intra-rectally to inhibit the transmission of the retrovirus.

4. The method of claim 1, wherein said compound is administered to a human as a pharmaceutical formulation.

5. The method of claim 1, wherein the contacting of said retrovirus with said compound is performed in a blood product, blood plasma, nutrient media, protein, a pharmaceutical, a cosmetic, a sperm or oocyte preparation, cells, cell cultures, bacteria, viruses, food or drink.

6. The method of claim 1, further comprising contacting said retrovirus with a non-thiolester anti-retroviral agent selected from the group consisting of zidovudine, dideoxycytidine 5-triphosphate and didanosine.

7. The method of claim 1, wherein the retrovirus is selected from an HIV-1, an HIV-2, an SIV, a BIV, an EIAV, a Visna, a CaEV, an HTLV-1, a BLV, an MPMV, an MMTV, an RSV, an MuLV, a FeLV, a BaEV, or an SSV retrovirus.

8. The method of claim 1, wherein said retrovirus is an HIV-1.

\* \* \* \* \*

UNITED STATES PATENT AND TRADEMARK OFFICE
CERTIFICATE OF CORRECTION

PATENT NO. : 7,625,917 B2
APPLICATION NO. : 10/738062
DATED : December 1, 2009
INVENTOR(S) : Turpin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1264 days.

Signed and Sealed this

Second Day of November, 2010

David J. Kappos
*Director of the United States Patent and Trademark Office*